United States Patent
Arunachalam et al.

(10) Patent No.: US 9,700,632 B2
(45) Date of Patent: Jul. 11, 2017

(54) DENDRIMERS, CONJUGATES AND METHODS THEREOF

(71) Applicant: Centre for BioSeparation Technology—VIT, Vellore, Tamil Nadu (IN)

(72) Inventors: Vijayalakshmi Mookambeswaran Arunachalam, Tamil Nadu (IN); Jisha John, Tamil Nadu (IN); Yves Marie Daniel Gnanou, Paris (FR); Vijayakrishna Kari, Tamil Nadu (IN)

(73) Assignee: CENTRE FOR BIOSEPERATION TECHNOLOGY-VIT, Vellore (IN)

( * ) Notice: Subject to any disclaimer, the term of this patent is extended or adjusted under 35 U.S.C. 154(b) by 0 days.

(21) Appl. No.: 14/428,210

(22) PCT Filed: Sep. 13, 2013

(86) PCT No.: PCT/IB2013/058534
§ 371 (c)(1),
(2) Date: Mar. 13, 2015

(87) PCT Pub. No.: WO2014/041517
PCT Pub. Date: Mar. 20, 2014

(65) Prior Publication Data
US 2015/0238623 A1    Aug. 27, 2015

(30) Foreign Application Priority Data
Sep. 13, 2012    (IN) .......................... 3797/CHE/2012

(51) Int. Cl.
*A01N 43/66* (2006.01)
*A61K 31/53* (2006.01)
*A61K 47/48* (2006.01)
*A61K 31/57* (2006.01)
*A61K 31/704* (2006.01)
*C08G 81/00* (2006.01)
*C08G 65/331* (2006.01)
*C08G 65/333* (2006.01)
*C08G 65/44* (2006.01)
*A61K 31/495* (2006.01)

(52) U.S. Cl.
CPC ........ *A61K 47/48215* (2013.01); *A61K 31/57* (2013.01); *A61K 31/704* (2013.01); *A61K 47/48061* (2013.01); *C08G 65/3314* (2013.01); *C08G 65/33317* (2013.01); *C08G 65/44* (2013.01); *C08G 81/00* (2013.01); *A61K 31/495* (2013.01); *A61K 31/53* (2013.01); *C08G 2650/32* (2013.01)

(58) Field of Classification Search
None
See application file for complete search history.

(56) References Cited

U.S. PATENT DOCUMENTS

| 5,342,940 A | 8/1994 | Ono et al. |
| 2002/0182172 A1 | 12/2002 | Bentley et al. |
| 2009/0287005 A1 | 11/2009 | Baker, Jr. et al. |

OTHER PUBLICATIONS

Karak et al. Journal of Polymer Science: Part A: Polymer Chemistry (2010), vol. 48, pp. 3994-4004.*
Konkolewicz et al. Marcromolecules (2011), vol. 44, pp. 7067-7087.*
Damodaran et al. European Pharmaceutical Review (2010), Issue 1, pp. 18-26.*
Cui-Fen et al. Reactive & Functional Polymers (2006), vol. 66, pp. 952-956.*
Feng et al., Bouquet-type Dendrimerliked Poly(ethylene Oxides)s with a Focal Aldehyde and Peripheral Hydroxyls, vol. 8, Biomacromolecules, pp. 2374-2378, Jul. 13, 2007. Retrieved from the Internet: <URL: http://pubs.acs.org/doi/abs/10.1021/bm070146r>.
International Searching Authority, International Search Report and Written Opinion for International Application No. PCT/IB2013/058534, Mar. 13, 2014, 22 pages.

* cited by examiner

*Primary Examiner* — Patrick Lewis
(74) *Attorney, Agent, or Firm* — McCoy Russell LLP

(57) ABSTRACT

The present disclosure relates to dendrimers composed of a hetero-bifunctional moiety and an aromatic heterocycle and to methods of synthesizing said dendrimers. The present disclosure also relates to dendrimer-bioactive molecule conjugates, the process of synthesizing the conjugates and pharmaceutical compositions comprising said conjugates. The dendrimer in the conjugates acts as a carrier and significantly increases the therapeutic efficacy of the bioactive molecule.

20 Claims, 16 Drawing Sheets

Succinylated PEG dendrimer with eight COOH groups at the periphery

DENDRIMERS, CONJUGATES AND METHODS THEREOF

CROSS REFERENCE TO RELATED APPLICATIONS

The present application is a national stage filing of PCT Patent Application No. WO 2014/041517 A2, filed on Sep. 13, 2013, and entitled DENDRIMERS, CONJUGATES AND METHODS THEREOF, which claims priority to Indian patent application serial number 3797/CHE/2012 filed on Sep. 13, 2012, the entire contents of which are incorporated by reference.

FIELD OF THE INVENTION

The present disclosure relates to dendrimers composed of a hetero-bifunctional moiety and an aromatic heterocycle, and methods of synthesizing said dendrimers. The present disclosure also relates to dendrimer-bioactive molecule conjugates, the process of synthesizing the conjugates, and pharmaceutical compositions comprising said conjugates. The dendrimer in the conjugates act as a carrier and significantly increases the therapeutic efficacy of the bioactive molecule.

BACKGROUND OF THE INVENTION

Cancer is the second leading cause of death worldwide. The most common form of cancer is prostate cancer and is known to be a leading cause of death among men world over. The current cancer therapies encounter challenges like non-specific systemic distribution of antitumor agents, inadequate drug concentrations reaching the tumor, and the toxic effects related to the chemotherapeutic drugs.

Prostate, lung, bronchus, colon and rectal cancer are known to be the most common forms of cancer. Though uncommon in Asian countries, the incidence is increasing even in India. A recent report showed that prostate cancer ranks $5^{th}$ in incidence and $4^{th}$ in cancer mortality for men in Mumbai, India. The incidence is increasing by 1% every year. Conventional anti-cancer drugs cause serious side effects and, at best, merely extend the patient's lifespan by few years. For example, doxorubicin causes damage to heart, Methotrexate causes liver damage and cisplatin is known to cause nephrotoxicity. Thus, there is a demand to utilize alternative concepts or approaches for the treatment of cancer.

Drugs derived from natural products make an enormous contribution to drug discovery today. Over 60% of approved chemotherapeutic agents and their sources are derived from natural compounds. More than 25% of drugs used during the last two decades are directly derived from plants, while the other 25% are chemically altered natural products. From approximately 250,000 higher plants, only 5-15% has ever been investigated for bioactive compounds.

Medicinal plants/herbs are known to be the most exclusive source of life saving drugs for a major population world over. They have been widely used for the treatment of diseases in traditional way for several generations. An interaction between traditional medicine and modern biotechnological tools is to be established towards new drug development. The strong evidences from epidemiological and experimental studies highlight the importance of compounds derived from plants "phytochemicals" to reduce the risk of cancer and also inhibit the development and spread of tumors in experimental animals. About 60% of the currently known anticancer drugs are either directly derived from natural source or are chemically altered natural products. The advantage of using such compounds for cancer treatment is their relatively non-toxic nature and less side effects.

Pentacyclic triterpenes are secondary plant metabolites present widely in fruit peel, leaves and stem bark and other. These triterpenes display various pharmacological effects being devoid of prominent toxicity. Lupeol, a triterpene is an anti-oxidant, anti-mutagenic compound having anti-inflammatory effects in in vitro and in vivo systems. Lupeol is also known to induce differentiation and inhibit the cell growth of mouse melanoma and human leukemia cells. Lupeol and its ester are shown to have a protective effect against cyclophosphamide induced cardiac damage by restoration of mitochondrial structure and function. It has also been shown that lupeol activates Fas receptor mediated apoptotic machinery of LNCaP cells and inhibits the tumorigenesis of prostate cancer cells in an animal model.

However, an increase in the efficacy and bioavailability of these compounds remain a major drawback due to the lack of efficient delivery systems. Thus, the present disclosure aims at overcoming the drawbacks of the prior art to increase the efficacy and bioavailability of bioactive molecules/drugs.

SUMMARY OF THE INVENTION

The present disclosure relates to a dendrimer composed of a hetero-bifunctional moiety and an aromatic heterocycle; a method of obtaining methoxy PEG generation 2 dendrimer having four active groups, said method comprising acts of: (a) reacting methoxy PEG with aromatic heterocycle to obtain methoxy PEG generation 1 dendrimer having two active groups, (b) reacting the dendrimer obtained in step (a) with dihydroxy PEG to obtain methoxy PEG generation 1.5 dendrimer having two active groups, and (c) reacting the dendrimer obtained in step (b) with an aromatic heterocycle to obtain the methoxy PEG generation 2 dendrimer having four active groups; a method of obtaining acetal PEG generation 2 dendrimer with eight active functional groups, said method comprising acts of: (a) reacting the 3,3-diethoxy-1,2-propanediol with an aromatic heterocycle to obtain acetal PEG generation 1 dendrimer with four active functional groups, (b) reacting the dendrimer obtained in step (a) with PEG to obtain an acetal PEG generation 1.5 dendrimer with four active groups, and (c) reacting the dendrimer obtained in step (b) with an aromatic heterocycle to obtain the acetal PEG generation 2 dendrimer with eight active functional groups; a conjugate comprising a dendrimer and a bioactive molecule, wherein the dendrimer is composed of a hetero-bifunctional moiety and an aromatic heterocycle; a method of obtaining a conjugate comprising a dendrimer and a bioactive molecule, wherein the dendrimer is composed of a hetero-bifunctional moiety and an aromatic heterocycle and optionally linked to targeting agent(s), said method comprising acts of: (a) synthesizing the dendrimer composed of a hetero-bifunctional moiety and an aromatic heterocycle optionally linked to targeting agent(s) and (b) conjugating the dendrimer optionally linked to targeting agent(s) obtained in step (a) with the bioactive molecule to obtain said conjugate; a pharmaceutical composition comprising a conjugate of a dendrimer and a bioactive molecule, optionally along with pharmaceutically acceptable excipients, wherein the dendrimer is composed of a hetero-bifunctional moiety and an aromatic heterocycle and optionally linked to targeting agent(s); a method of inducing/increasing cytotoxicity in cancer cells, said method comprising act of incubating the cancer cells with a conjugate comprising a dendrimer and a bioactive molecule or a composition comprising a dendrimer and a bioactive molecule, wherein the dendrimer is optionally linked to targeting agent(s) and is composed of a hetero-bifunctional moiety and an aromatic heterocycle; a method of treating a subject having or suspected of having cancer, said method comprising act of administering a conjugate comprising a dendrimer and a bioactive molecule or a composition thereof, to the subject in need thereof, wherein the dendrimer is optionally linked to targeting agent(s) and is composed of a hetero-bifunctional moiety and an aromatic heterocycle.

BRIEF DESCRIPTION OF THE DRAWINGS

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where.

DETAILED DESCRIPTION OF THE PREFERRED EMBODIMENTS

Figure 1:
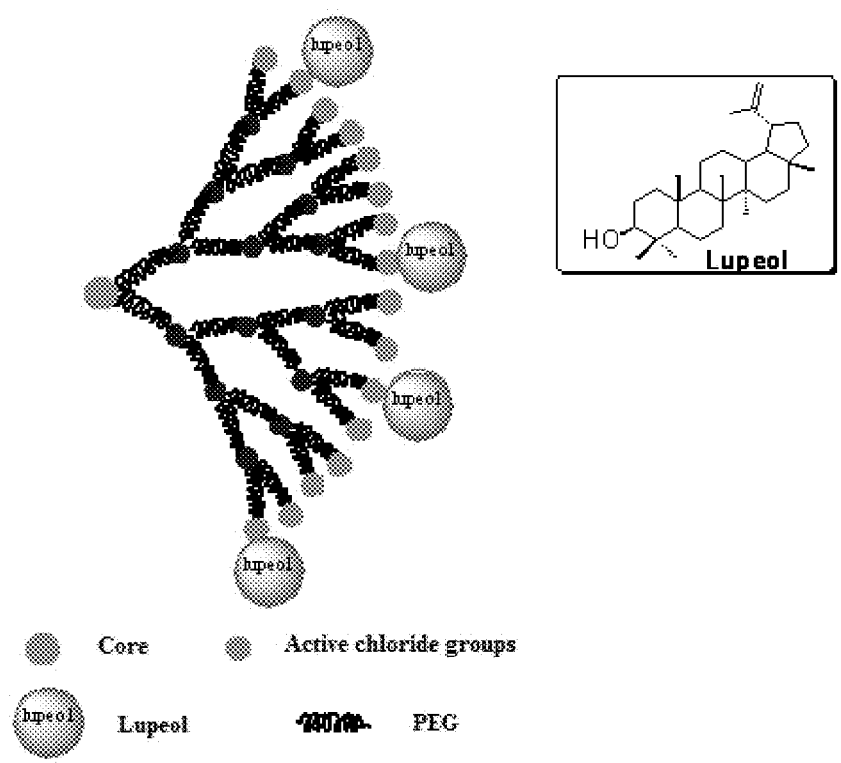
FIG. 1 illustrates schematic representation of the final dendrimer-lupeol conjugate system used for delivery.

The present disclosure relates to a dendrimer composed of a hetero-bifunctional moiety and an aromatic heterocycle.

In another embodiment of the present disclosure, the hetero-bi functional moiety is selected from a group comprising mPEG-COOH, mPEG-NH$_2$, monomethoxy PEG, 3,3-Dimethoxy-1,2-propanediol and 3,3-diethoxy-1,2-propanediol; and wherein the aromatic heterocycle is selected from a group comprising triazine trichloride and 2,4,6-trifluoro-1,3,5-triazine.

In an embodiment of the present disclosure, the dendrimer is represented by the formula shown in structure I

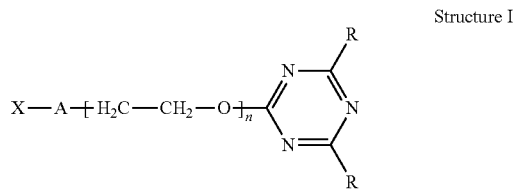

Structure I wherein,

'X' is a methyl group, a 3,3-diethoxypropanedioxy fragment [(EtO)$_2$—CH$_2$—CH(O)—CH$_2$O], a 3,3-Dimethoxypropanedioxy fragment [(CH$_3$O)$_2$—CH$_2$—CH(O)—CH$_2$O];

'A' is an Oxygen atom;

n is 1-500, and

R is selected from a group comprising Cl, F, —OH and $R_d$, wherein $R_d$ is represented by the formula shown in structure II $R_d$ is

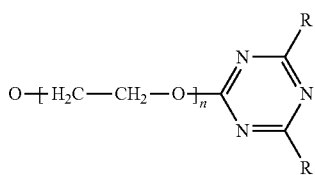

Structure II wherein, R in structure I is Cl, F or —OH when the dendrimer is of a generation 1 or generation 1.5, and R is $R_d$ when the dendrimer is of generation 2-10;

wherein the dendrimer of all generation(s) have active functional group selected from a group comprising Cl, F or —OH in the periphery.

In an embodiment of the present disclosure, the dendrimer is of generation selected from 1, 1.5, 2, 2.5, 3, 3.5, 4, 4.5, 5, 5.5, 6, 6.5, 7, 7.5, 8, 8.5, 9, 9.5 and 10.

In an embodiment of the present disclosure, the generation of dendrimers contain 2, 4, 8, 16, 32, 64, 128, 256, 512 or 1024 active functional groups.

In an embodiment of the present disclosure, the said dendrimer comprise a core unit and a branching unit, wherein the core unit is selected from a group comprising mPEG-COOH, mPEG-NH$_2$, monomethoxy PEG, 3,3-Dimethoxy-1,2-propanediol and 3,3-diethoxy-1,2-propanediol; and wherein the branching unit is selected from a group comprising aromatic heterocycle, polyethylene glycol, dihydroxy PEG and combination thereof, wherein the aromatic heterocycle is selected from a group comprising triazine trichloride and 2,4,6-trifluoro-1,3,5-triazine.

The present disclosure also relates to a method of obtaining methoxy PEG generation 2 dendrimer having four active groups, said method comprising acts of:

a) reacting methoxy PEG with aromatic heterocycle to obtain methoxy PEG generation 1 dendrimer having two active groups;

b) reacting the dendrimer obtained in step (a) with dihydroxy PEG to obtain methoxy PEG generation 1.5 dendrimer having two active groups; and c) reacting the dendrimer obtained in step (b) with aromatic heterocycle to obtain the methoxy PEG generation 2 dendrimer having four active groups.

The present disclosure also relates to a method of obtaining acetal PEG generation 2 dendrimer with eight active functional groups, said method comprising acts of:

a) reacting the 3,3-diethoxy-1,2-propanediol with aromatic heterocycle to obtain acetal PEG generation 1 dendrimer with four active functional groups;

b) reacting the dendrimer obtained in step (a) with PEG to obtain acetal PEG generation 1.5 dendrimer with four active groups; and c) reacting the dendrimer obtained in step (b) with aromatic heterocycle to obtain the acetal PEG generation 2 dendrimer with eight active functional groups.

In an embodiment of the present disclosure, the aromatic heterocycle is selected from triazine trichloride and 2,4,6-trifluoro-1,3,5-triazine.

In an embodiment of the present disclosure, the active functional groups are selected from a group comprising hydroxyl group (—OH), chloride and fluoride.

In an embodiment of the present disclosure, the reaction is carried out in presence of sodium bicarbonate and toluene.

The present disclosure also relates to a conjugate comprising dendrimer and bioactive molecule, wherein the dendrimer is composed of a hetero-bifunctional moiety and an aromatic heterocycle.

In an embodiment of the present disclosure, the hetero-bifunctional moiety is selected from a group comprising mPEG-COOH, mPEG-NH$_2$, monomethoxy Poly Ethylene Glycol, and 3,3-diethoxy-1,2-propanediol; and wherein the aromatic heterocycle is selected from a group comprising triazine trichloride, and 2,4,6-trifluoro-1,3,5-triazine.

In an embodiment of the present disclosure the dendrimer is represented by the formula shown in structure I

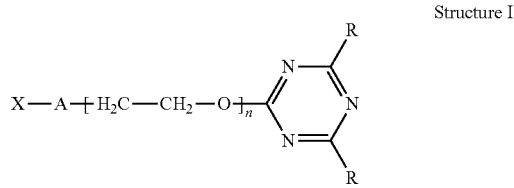

Structure I wherein,

'X' is a methyl group, a 3,3-diethoxypropanedioxy fragment [(EtO)$_2$—CH$_2$—CH(O)—CH$_2$O,] a 3,3-Dimethoxypropanedioxy fragment [(CH$_3$O)$_2$—CH$_2$—CH(O)—CH$_2$O;

'A' is an Oxygen atom;

n is 1-500, and

R is selected from a group comprising Cl, F, —OH and $R_d$, wherein $R_d$ is represented by the formula shown in structure II

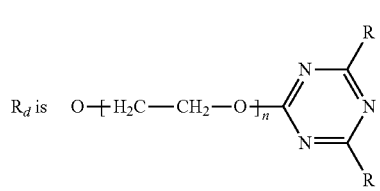

Structure II wherein, R in structure I is Cl, F or —OH when the dendrimer is of generation 1 or generation 1.5, and R is $R_d$ when the dendrimer is of generation 2-10;

wherein the dendrimer of all generation(s) have active functional group selected from a group comprising Cl, F or —OH in the periphery.

In an embodiment of the present disclosure, the structure of a generation 2 dendrimer having trizaine trichloride as the aromatic heterocycle is depicted in the formula shown in structure III

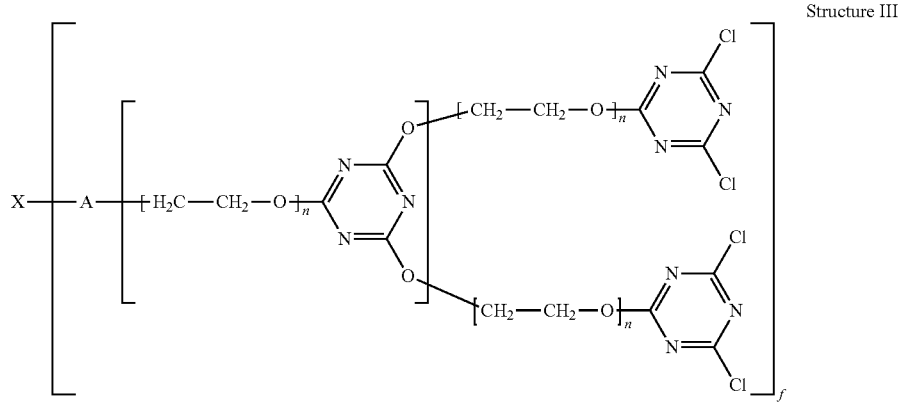

Structure III wherein, 'X' is a methyl group;
'A' is an Oxygen atom;
F is 1; and
n is 1-500.

In an embodiment of the present disclosure the bioactive molecule is covalently attached within the dendrimer or onto the dendrimer surface, or a combination thereof.

In an embodiment of the present disclosure the dendrimer is optionally linked to targeting agent(s).

In an embodiment of the present disclosure, the targeting agents are selected from a group of agents that bind to receptors.

In an embodiment of the present disclosure, the targeting agents are selected from a group comprising monoclonal antibodies, vitamins, peptides, and polysaccharides specific for receptors concentrated on the surface of cells associated with the disease and other conventionally known targeting agents.

In an embodiment of the present disclosure, the targeting agent is folic acid.

The present disclosure also relates to a method of obtaining a conjugate comprising a dendrimer and a bioactive molecule, wherein the dendrimer is composed of a hetero-bifunctional moiety and an aromatic heterocycle and optionally linked to targeting agent(s), said method comprising acts of:
a) synthesizing the dendrimer composed of hetero-bifunctional moiety and aromatic heterocycle optionally linked to targeting agent(s); and
b) conjugating the dendrimer optionally linked to targeting agent(s) obtained in step (a) with the bioactive molecule to obtain said conjugate.

The present disclosure also relates to a pharmaceutical composition comprising a conjugate of a dendrimer and a bioactive molecule, optionally along with pharmaceutically acceptable excipients, wherein the dendrimer is composed of a hetero-bifunctional moiety and an aromatic heterocycle and optionally linked to targeting agent(s).

In an embodiment of the present disclosure, the pharmaceutical composition is in the form of a pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

In an embodiment of the present disclosure, the non-limiting examples of pharmaceutically-acceptable excipients suitable for use in the present disclosure include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, plant cellulosic material and spheronization agents, and any combination thereof. In an embodiment of the present disclosure, the bioactive molecule is selected from a group comprising lupeol, lupeol derivative, doxorubicin, betulinic acid, betulin derivative, cisplatin, camptothecin, paclitaxel and any combination thereof.

The present disclosure also relates to a method of inducing/increasing cytotoxicity in cancer cells, said method comprising act of incubating the cancer cells with a conjugate comprising a dendrimer and a bioactive molecule or a composition comprising a dendrimer and a bioactive molecule, wherein the dendrimer is optionally linked to targeting agent(s) and is composed of a hetero-bifunctional moiety and an aromatic heterocycle.

The present disclosure also relates to a method of treating a subject having or suspecting of having a disease, said method comprising act of administering a conjugate comprising a dendrimer and a bioactive molecule or a composition thereof, to the subject in need thereof, wherein the dendrimer is optionally linked to targeting agent(s) and is composed of a hetero-bifunctional moiety and an aromatic heterocycle.

The present disclosure also relates to a method of treating a subject having or suspecting of having cancer, said method comprising act of administering a conjugate comprising a dendrimer and a bioactive molecule or a composition thereof, to the subject in need thereof, wherein the dendrimer is optionally linked to targeting agent(s) and is composed of a hetero-bifunctional moiety and an aromatic heterocycle.

PEG (Polyethylene glycol) is also known in the art as polyethylene oxide (PEO). Hence, the term PEG and PEO are used interconvertably in the present disclosure.

Poly(ethylene oxide) [PEO] have many potential applications in biomedical and pharmaceutical areas owing to its water solubility, non toxicity, ion-transporting ability, and non-recognition by the immune system along with the presence of functional groups that permit the covalent attachment of biologically active molecules. These carriers are capable of increasing water solubility of biologically active components and improve its stability against enzymatic degradation and facilitates their pharmacological administration. Low molar mass linear PEO suffers from its inherent low loading capacities. The linear PEO polymers consist of only one or at the most two reacting sites depending upon the nature of the end groups.

In one embodiment, the present disclosure provides a targeted therapy exploiting the potential of plant based active component by use of a hetero-bifunctional moiety and aromatic heterocycle based dendrimers as the carrier for enhanced therapeutic efficacy.

In one embodiment, the present disclosure provides a targeted therapy exploiting the potential of plant based active component by use of hetero-bifunctional poly(ethylene oxide) [PEO] and triazine based dendrimers as the carrier for enhanced therapeutic efficacy.

In an embodiment, triazine chloride (also called cyanuric chloride) is employed by the present disclosure as its aromatic ring carries free chloride groups that can undergo nucleophilic substitution in the presence of nucleophiles, this occurring sequentially in temperature dependent manner and using this chemistry, new generations of PEG can be hooked and the synthesis of dendrimers are carried out.

In an embodiment, the present disclosure relates to the synthesis of hetero-bifunctional bouquet type G2 dendrimers with methoxy group on one hand and active chloride groups on the other hand which is covalently attached to bioactive molecules. To evaluate the usefulness of these dendrimers for increased activity of plant based bioactive molecule, lupeol is covalently coupled to second generation (G2) dendrimer containing four active chloride groups at the periphery for easy conjugation (FIG. 1). The high level of control over the structure of dendrimers of the present disclosure, their size, shape, branching length/density, and their surface functionality, clearly establishes these structures as unique and efficient drug carriers.

In an embodiment of the present disclosure, lupeol is used as the bioactive molecule in the 'dendrimer-bioactive molecule conjugate' as a proof of concept and the bioactive molecules can be extended to other known plant based bioactive molecules such as but not limited to betulinic acid, betulin known for their anticancer activity and to other well-known chemotherapeutic drugs like doxorubicin, cisplatin, camptothecin, paclitaxel by modifying the polymer and/or drug as required. These dendrimer-bioactive molecule conjugates increase the therapeutic effect of the bioactive molecules.

In an embodiment of the present disclosure, the bioactive molecule is not limiting only to bioactive molecules showing anti-cancer activity, but any bioactive molecule which shows therapeutic effect or for achieving desired effect.

In another embodiment of the present disclosure, the bioactive molecules can either be encapsulated into the interior of the dendrimers or chemically attached or physically adsorbed onto the dendrimer surface, with the option of modifying the dendrimer to the specific needs of the bioactive molecule and its therapeutic applications. In an exemplary embodiment of the present disclosure, the bioactive molecule is covalently attached to the dendrimer and hence increasing the cytotoxic effect of the same.

In another embodiment of the present disclosure, the dendrimer conjugates allow targeted therapy by coupling molecules specific to the target on the cell surface on one hand and chemotoxic active molecule on the second function. Targeted therapy along with the use of plant based anticancer molecule ensures less side effects as compared to the present cancer therapies.

In another embodiment of the present disclosure, the dendrimers of the lupeol-dendrimer conjugates allow targeted therapy by coupling antibody specific to the target cell surface antigen on one hand and chemotoxic active molecule on the second function.

In an embodiment, the cytotoxic activity (MTT assay) on human prostate cancer cell line PC3 cell lines show that there is a significant increase in the cytotoxic activity of the dendrimer conjugates when compared to free bioactive molecule.

Figure 7:
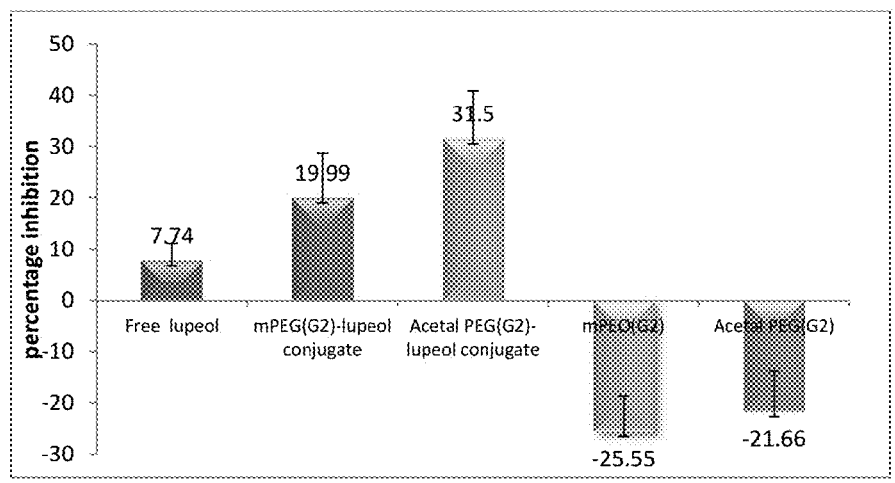
FIG. 7 illustrates comparative cytotoxic effects of free lupeol, mPEG(G2)-lupeol conjugate, acetal PEG(G2)-lupeol conjugate, mPEG(G2) dendrimer alone and acetal PEG(G2) dendrimer alone at 10 μg/ml and 48 hours of treatment. The results depicted are average of two experiments done in triplicates.
Figure 8A:
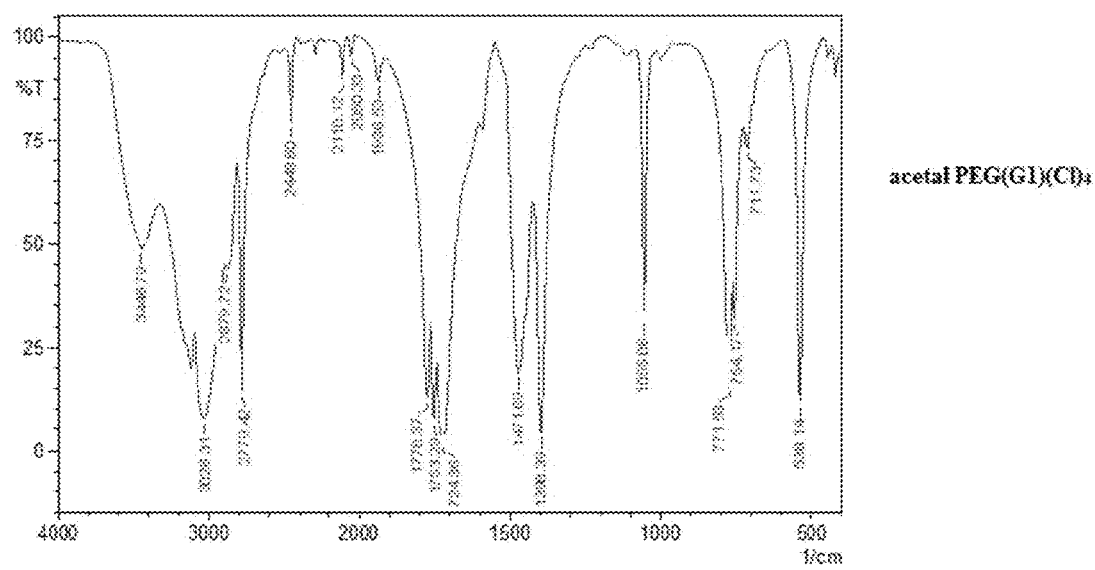
FIGS. 8A-8C illustrate FTIR spectrums for the different generations of dendrimers with 3,3-diethoxy-1,2-propanediol as a core, with acetal PEG(G1)(Cl)$_4$ shown in FIG. 8A, acetal PEG (G1.5)(HO)$_4$ shown in FIG. 8B, and acetal PEG(G2)(Cl)$_8$ shown in FIG. 8C.
Figure 8B:
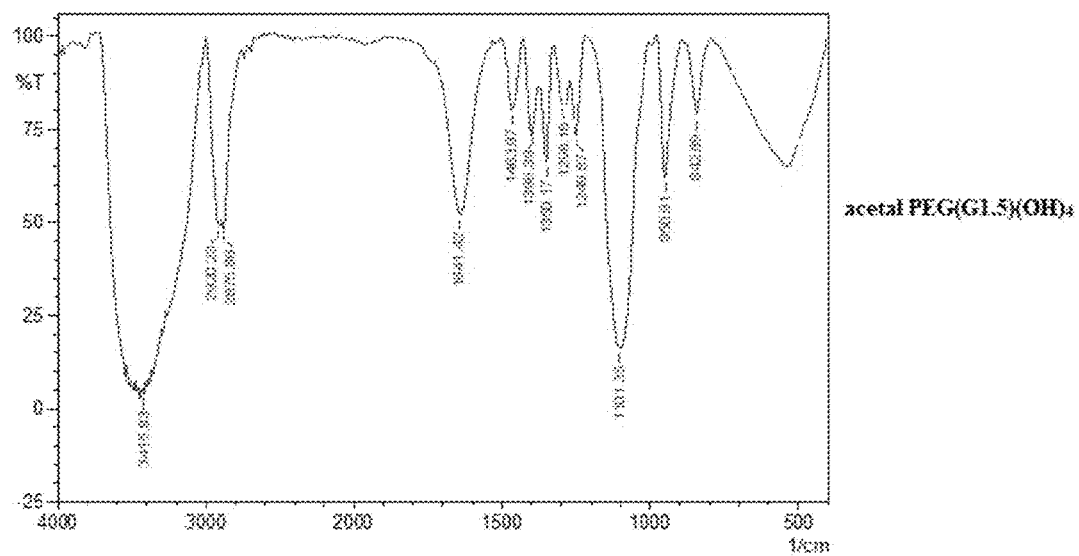
Figure 8C:
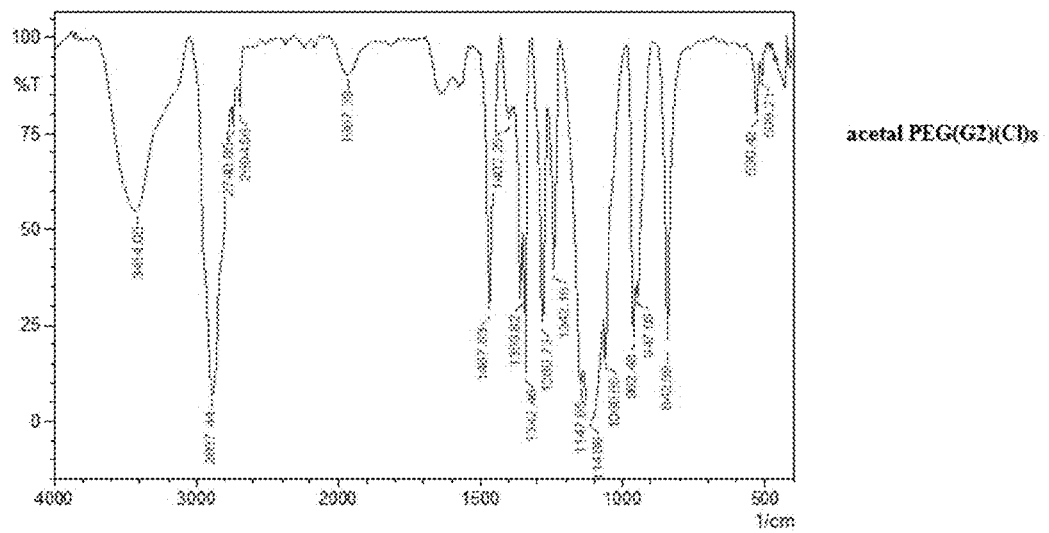

In an embodiment, the cytotoxic activity (MTT assay) on human prostate cancer cell line PC3 cell lines show that there is a significant increase in the cytotoxic activity of the lupeol-dendrimer conjugates when compared to free lupeol (FIG. 7).

In an embodiment of the present disclosure, the dendrimers, after disassociation from the bioactive molecule-dendrimer conjugate, are easily secreted into urine or cleared through liver. Thus, the dendrimers of the present disclosure are non-toxic in nature along with their efficiency in significantly improving the activity of bioactive molecule.

Additional embodiments and features of the present disclosure will be apparent to one of ordinary skill in art based upon description provided herein. However, the examples and the figures should not be construed to limit the scope of the present disclosure.

Materials Used for Arriving at the Examples Provided within the Ambit of the Instant Disclosure Monomethoxypoly(ethylene oxide) (5000), 3,3-diethoxy-1-propene, N-Methylmorpholine-N-Oxide (NMO), Osmium tetraoxide ($OsO_4$) Polyethylene(ethylene oxide) (3350), Lupeol standard, Cyanuric chloride(2,4,6-trichloro-s-triazine), Thiazol tetrazolium blue (MTT reagent) are purchased from sigma aldrich. Sodium carbonate, ethyl ether, acetone, t-butanol, toluene, petroleum ether (boiling range, 35-60° C.) purchased from Qualigens fine chemicals (India) dried over $CaH_2$ prior to use. Column chromatography and TLC are carried out using Qualigens fine chemical silica gel 60 and Merk precoated silica gel 60 plates, respectively.

Example 1

Synthesis of Bouquet Type Dendrimer with MethoxyPEG(mPEG) as Core

Synthesis of monomethoxy poly(ethylene oxide) core based dendrimers having both dihydroxy poly(ethylene oxide) and triazine trichloride as branching units in their structural frame is done for covalent attachment of plant based anticancer component lupeol and thereby increasing its cytotoxic activity. The synthesis is done with divergent approach with monomethoxy poly(ethylene oxide) as core. The synthesis procedure (FIG. 2) is as follows:

(A) Synthesis of $mPEG(G1)(Cl)_2$ 25 g (5 m mol) of monomethoxy PEG(5000) dissolved in 10 ml of methanol is added slowly to 2.76 g (15 m mol) of Cyanuric chloride in 300-500 mL of anhydrous toluene containing 5 g of anhydrous sodium bicarbonate at 0° C.-4° C. The solution is stirred initially for 2-4 hours (h) at 0° C.-4° C., then for 2-4 hours at room temperature (RT) [25° C.-30° C.] and refluxed with stirring at 70° C.-80° C.±2° C. for 48-60 hours. The reaction mixture is filtered and concentrated. The final product [$mPEG(G1)(Cl)_2$] is purified by washing with diethyl ether to remove the unreacted cyanuric chloride. The progress of the reaction is monitored using thin layer chromatography (TLC).

(B) Synthesis of mPEG(G1.5)(OH)$_2$ 23.42 g (6.94 mmol) of dihydroxy PEG(3350) dissolved in 50 ml methanol is added slowly to 18 g of mPEG(G1)(Cl)$_2$ dissolved in 100-150 mL of anhydrous toluene containing 1.5-3.0 grams of anhydrous NaHCO$_3$, at 0° C.-4° C. The solution is stirred initially for 2-4 hours at 0° C.-4° C., then for 2-4 hours at RT and refluxed with stirring at 70° C.-80° C. for 24-36 hours. The reaction mixture is filtered and concentrated to obtain mPEG(G1.5)(OH)$_2$. Unreacted PEG is removed by carrying out dialysis for 6-10 hours against water at RT. The precipitate is collected and lyophilized.

(C) Synthesis of mPEG (G2)(Cl)$_4$ 12 g (1 mmol) of mPEG (G1.5)(OH)$_2$ dissolved in methanol is added to 0.553(3 mmol) of cyanuric chloride dissolved in 100-150 ml of anhydrous toluene containing 2-5 grams of sodium bicarbonate at 0° C.-4° C. The solution is stirred for 2-4 hours at 0° C.-4° C., for 2-4 hours at RT and then refluxed with stirring 70°-80° C.±2° C. for 48-60 hours. The reaction is monitored using TLC. The reaction mixture is filtered and concentrated. The final product [mPEG (G2)(Cl)$_4$] is purified by washing with diethyl ether to remove unreacted cyanuric chloride.

(D) Coupling of Lupeol to the mPEG (G2)(Cl)$_4$ 3 mg of lupeol dissolved in 1 ml of methanol is added to 20 mg of mPEG (G2)(Cl)$_4$ dissolved in 10-15 ml of anhydrous toluene containing 60-100 mg of sodium bicarbonate. The solution is stirred at room temperature for 72-80 hours, filtered and concentrated.

Results

Synthesis of monomethoxy poly(ethylene oxide) core based dendrimers having both dihydroxy poly(ethylene oxide) and triazine trichloride as branching units in their structural frame is carried out for covalent attachment of plant based anticancer component lupeol. The synthesis is carried out with divergent approach with monomethoxy poly(ethylene oxide) as core. The reaction is based on the addition of hydroxyl group of the core with the active chlorides of the triazine in the presence of sodium bicarbonate. In the first step, 1 equivalent of mPEG is allowed to react with 3 equivalents of cyanuric chloride to give a white, solid product [mPEG(G1)(Cl)$_2$]. In this step purification is done by washing the reaction mixture with diethyl ether to remove the excess of cyanuric chloride. The second step involves the addition of dihydroxy PEG(3350), wherein 2 equivalents of PEG(3350) is reacted with 1 equivalent of mPEG(G1)(Cl)$_2$. Purification is done by dialysis of the product against water. To increase the generation, triazine is allowed to react with dendrimer G1 at room temperature. All reactions are carried out in the presence of sodium bicarbonate (NaHCO$_3$) to provide the basic conditions required for the reaction and thus neutralizing the released hydrochloric acid (HCl).

Figure 2:
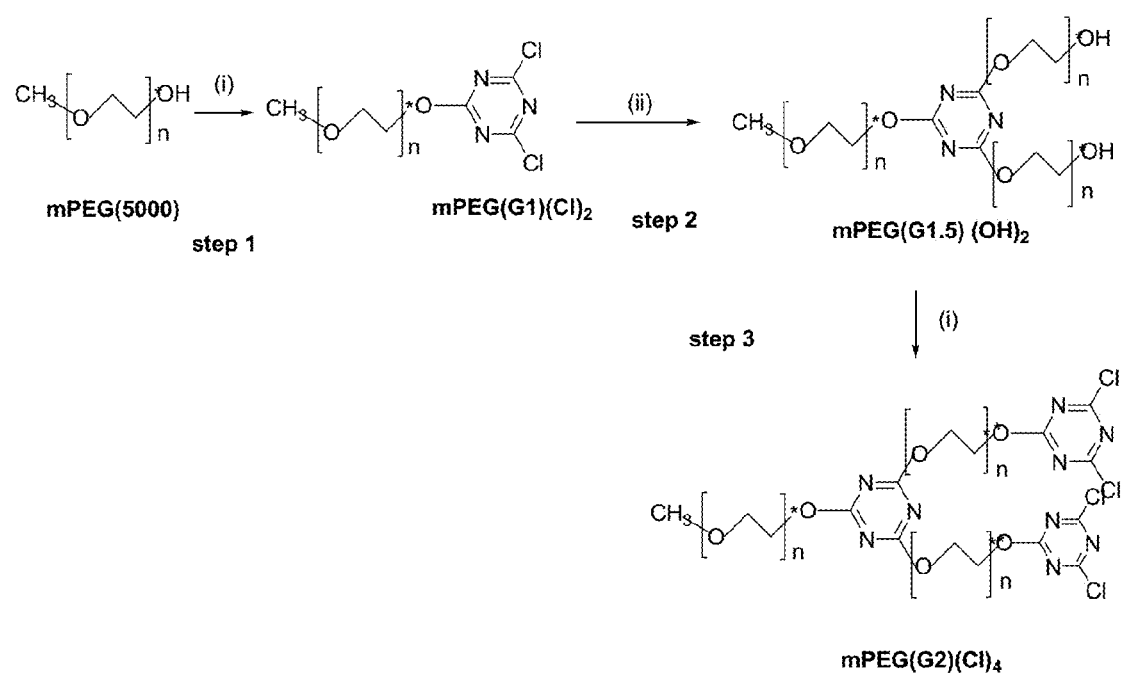
FIG. 2 illustrates the overall synthetic scheme for preparation of mPEG(G2)Cl$_4$ dendrimer with monomethoxy poly (ethylene oxide) as a core, and both triazine trichloride and dihydroxy poly(ethylene oxide) as branching units.

The preparation of mPEG(G2)Cl$_4$ dendrimer with monomethoxy poly(ethylene oxide) as a core, and both triazine trichloride and dihydroxy poly(ethylene oxide) as branching units is further well illustrated in FIG. 2 which depicts the following:

Step 1: Synthesis of mPEG(G1)(Cl)$_2$ dendrimer by addition of cyanuric chloride to the core i.e monomethoxy poly ethylene(oxide) in the presence of NaHCO$_3$ and Toluene as solvent, stirred at 0° C. for 2 hours, at RT for 2 hours, refluxed at 70° C.±2° C. for 48 hours.

Step 2: Synthesis of mPEG(G1.5)(OH)$_2$ dendrimer by addition of dihydroxy PEG(3350) to the mPEG(G1)(Cl)$_2$ in the presence of NaHCO$_3$ and Toluene as solvent, stirred at 0° C. for 2 hours, at RT for 2 hours, refluxed at 70°±2° C. for 24 hours.

Step 3: Synthesis of mPEG(G2)(Cl)$_4$ dendrimer by addition of cyanuric chloride to PEO(G1.5)(OH)$_2$ in the presence of NaHCO$_3$ and Toluene as solvent, stirred at 0° C. for 2 hours, at RT for 2 hours, refluxed at 70°±2° C. for 48 hours.

Figure 3:
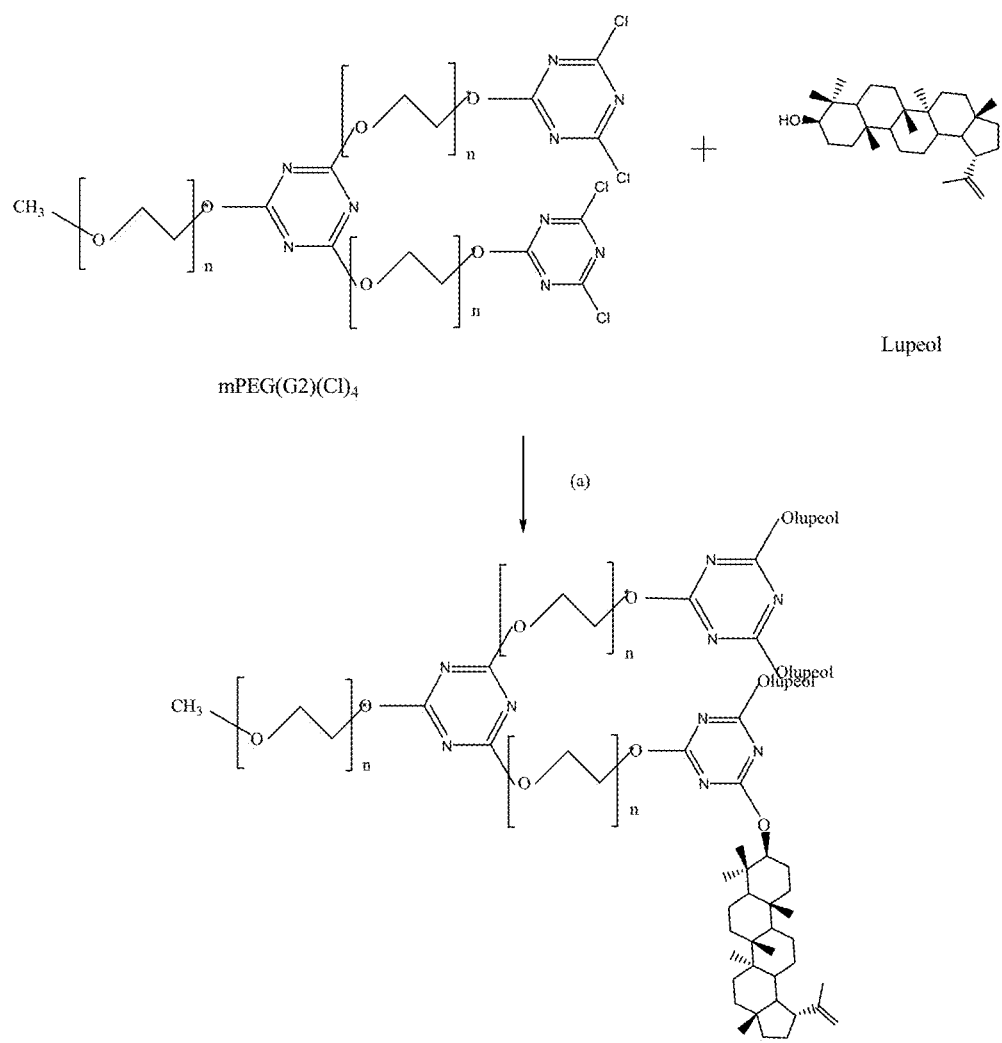
FIG. 3 illustrates coupling of lupeol to mPEG(G2)(Cl)$_4$ dendrimer by reacting lupeol with mPEG(G2)(Cl)$_4$ dendrimer dissolved in toluene in the presence of NaHCO$_3$ and stirred at room temperature for 72 hours.

The conjugation of synthesized mPEG(G2)(Cl)$_4$ dendrimer and lupeol is shown in FIG. 3 which depicts the reaction of lupeol and the mPEG(G2)(Cl)$_4$ dendrimer dissolved in toluene in the presence of NaHCO$_3$ and stirred at room temperature for 72 hours.

Example 2

Synthesis of bouquet type dendrimer with 3,3-diethoxy-1,2-propanediol as core

Synthesis of bouquet type dendrimer having both dihydroxy poly(ethylene oxide) and triazine trichloride as branching units in their structural frame is done for covalent attachment of plant based anticancer component lupeol and thereby increasing its cytotoxic activity. The synthesis is done with divergent approach with 3,3-diethoxy-1,2-propanediol as core.

Figure 4:
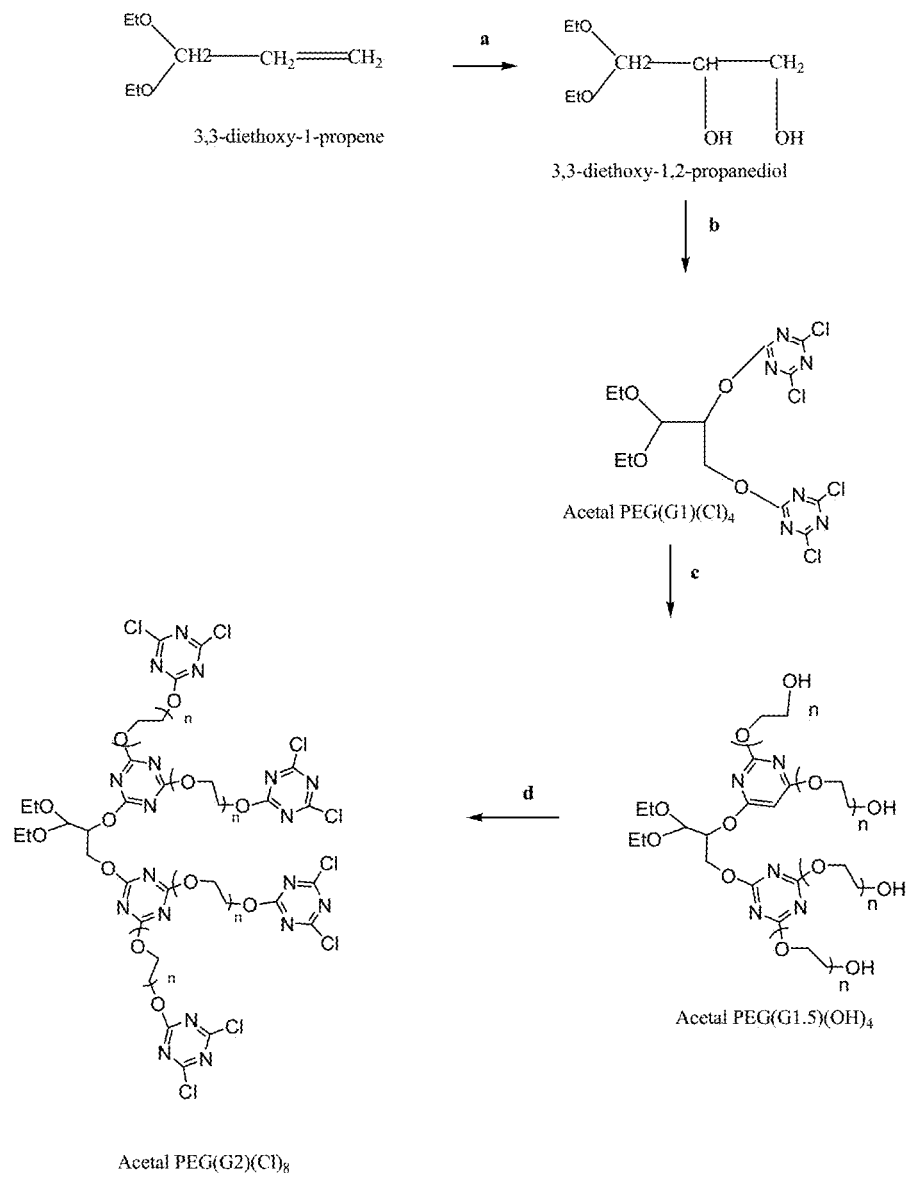
FIG. 4 illustrates overall synthetic scheme for preparation of acetal-PEG(G2)(Cl)$_8$ dendrimer with 3,3-diethoxy-1,2-propanediol as a core, and both triazine trichloride and dihydroxy poly(ethylene oxide) as branching units.

The synthesis procedure (FIG. 4) is as follows:

(A) Conversion of 3,3-ditheoxy-1-propene to 3,3-diethoxy-1,2-propanediol

To 3,3-ditheoxy-1-propene (15.2 ml), NMO (13.8 g), t-butanol (10 ml), acetone (40 ml), water (40 ml) is added at RT. In the presence of N$_2$, osmium tetroxide (OsO$_4$) (2 ml) is added to this solution. The solution is stirred for 48-60 hours at RT. The organic solvents are removed under vacuum, concentrated and extracted several times using CH$_2$Cl$_2$. The organic layers are collected and concentrated to obtain 3,3-diethoxy-1,2-propanediol. The reaction is monitored using TLC.

(B) Synthesis of acetal PEG(G1)(Cl)$_4$ 3,3-diethoxy-1,2-propanediol (10.74 g) is added to a solution of cyanuric chloride (35 g, 0.19 mol) in toluene containing 5-10 grams sodium bicarbonate at 0°-4° C. The solution is stirred for 1.5-3 hours at 0° C.-4° C., 1.5-3 hours at RT, and then refluxed with stirring at 70° C.-80° C.±2° C. for 48-60 hours. The solution is filtered and concentrated. The final product [acetal PEG(G1)(Cl)$_4$] is purified by washing with diethyl ether to remove the unreacted cyanuric chloride. The progress of the reaction is monitored using TLC.

(C) Synthesis of acetal PEG(G1.5)(OH)$_4$

To 400 mg (0.784 mmol) of acetal PEG(G1)(Cl)$_4$ in 100-150 ml of THF containing 3-4 grams of NaHCO$_3$, 16.04 grams (4.78 mmol) of PEG(3350) dissolved in 50 ml methanol is added slowly at 0°-4° C. The solution is stirred for 2-4 hours at 0° C.-4° C., for 2-4 hours at RT and then refluxed with stirring at 70° C.-80° C.±2° C. for 24-36 hours. The solution is filtered and concentrated to obtain acetal PEG (G1.5)(OH)$_4$. Unreacted PEG is removed by dialysis for 6 hours against water at RT. The precipitate is collected and lyophilized.

(D) Synthesis of acetal PEG(G2)(Cl)$_8$ 2 g (0.143 mmol) of acetal PEG(G1.5)(OH)$_4$ dissolved in methanol is added slowly to 159 mg (0.861 mmol) of cyanuric chloride dissolved in 100-150 ml toluene containing 1-1.5 grams NaHCO$_3$ at 0° C.-4° C. The solution is stirred for 1.5-3 hours at 0° C.-4° C., 1.5-3 hours at RT, and then refluxed with stirring at 70° C.-80° C.±2° C. for 48-60 hours. The solution is filtered and concentrated. The final product [acetal PEG(G2)(Cl)$_8$] is purified by washing with diethyl ether to remove the unreacted cyanuric chloride.

(E) Coupling of Lupeol to Acetal PEG(G2)(Cl)$_8$ 4 mg of lupeol dissolved in 1 ml of methanol is added to 20 mg of acetal PEG(G2)(Cl)$_8$ dissolved in 10-15 ml of anhydrous toluene in the presence of 60-80 mg of sodium bicarbonate. The solution is stirred at room temperature for 72-80 hour, filtered and concentrated.

Results

Synthesis of 3,3-diethoxy-1,2-propanediol core based dendrimers having both dihydroxy poly(ethylene oxide) and triazine trichloride as branching units in their structural frame is carried out for covalent attachment of plant based anticancer component lupeol. In this case, as the core used has two hydroxyl groups on the periphery, the second generation dendrimer i.e. acetal PEG(G2) has eight active chloride groups at the periphery available for conjugation. The preparation of Acetal PEG(G2)(Cl)$_8$ dendrimer with 3,3-diethoxy-1,2-propanediol as a core is further well illustrated in FIG. 4 which showcases the following:

Step (a): Conversion of 3,3-diethoxy-1-propene to 3,3-diethoxy-1,2-propanediol in the presence of N-Methylmorpholine-N-Oxide (NMO), acetone, water, t-butanol and OsO$_4$ [OsO$_4$ is added in the presence of N$_2$]. The reaction mixture is stirred at RT for 24-48 h or 48-60 h, preferably 24 h.

Step (b): Synthesis of acetal PEG(G1)(Cl)$_4$ dendrimer by addition of cyanuric chloride to the core i.e 3,3-diethoxy-1,2-propanediol in the presence of NaHCO$_3$ and toluene as solvent, stirred at 0° C. for 2 h, at RT for 2 h, refluxed at 70° C.±2° C. for 48 h.

Step (c): Synthesis of acetal PEG(G 1.5)(OH)$_4$ dendrimer by addition of PEG(3350) to the acetal PEG(G1)(Cl)$_4$ in the presence of NaHCO$_3$ and toluene as solvent, stirred at 0° C. for 2 h, at RT for 2 h, refluxed at 70±2° C. for 24 h.

Step (d): Synthesis of acetal PEG(G2)(Cl)$_8$ dendrimer by addition of cyanuric chloride to PEO(G1.5)(OH)$_2$ in the presence of NaHCO$_3$ and toluene as solvent, stirred at 0° C. for 2 h, at RT for 2 h, refluxed at 70°±2° C. for 48 h.

Figure 5:
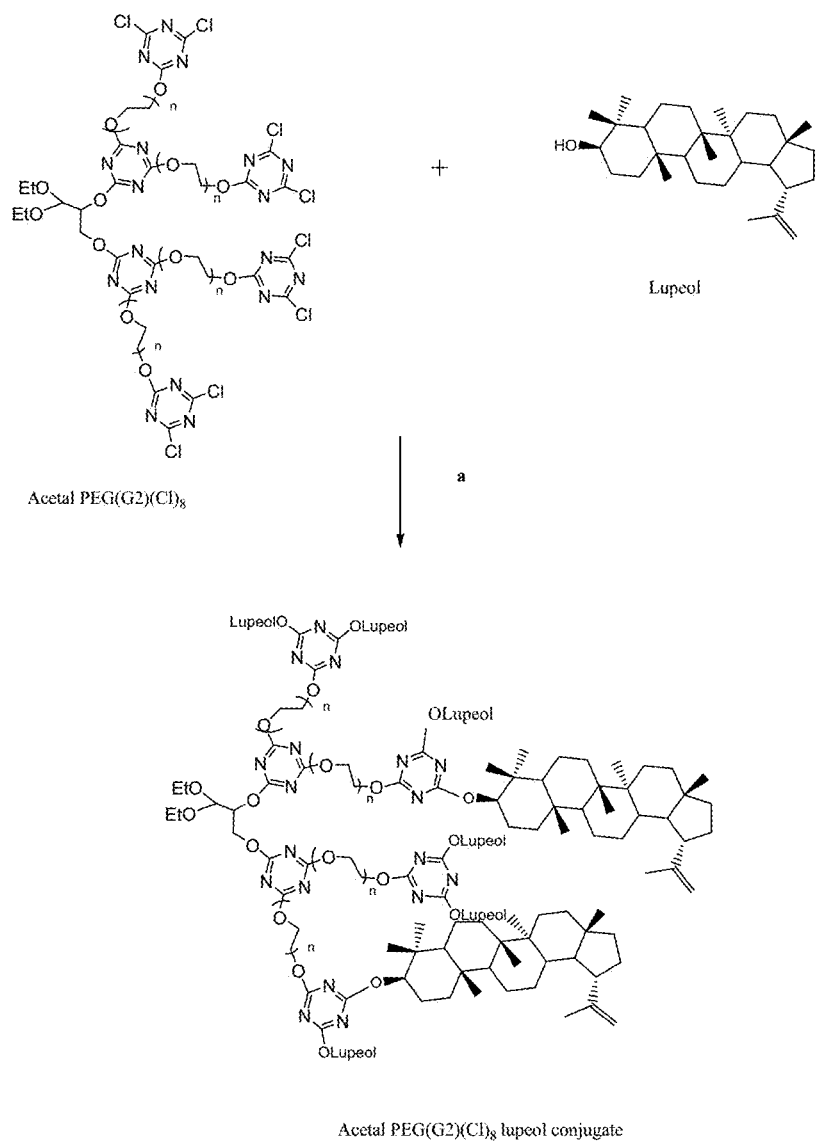
FIG. 5 illustrates coupling of the lupeol to acetal PEG (G2)(Cl)$_8$ dendrimer by reacting lupeol with acetal PEG(G2) (Cl)$_8$ dendrimer dissolved in toluene in the presence of NaHCO$_3$ and stirred at room temperature for 72 hours.
Figure 6A:
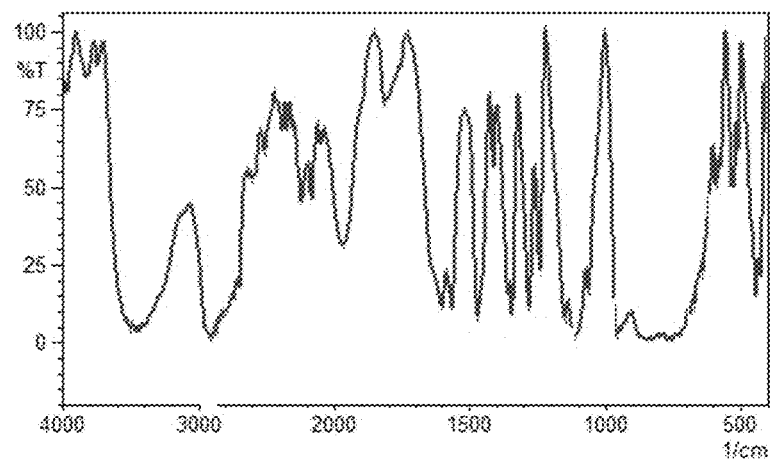
FIGS. 6A-6D illustrate FTIR spectrums for the different generations of dendrimers with methoxy PEG (mPEG) as a core, with mPEG(5000) shown in FIG. 6A, mPEG(G1)(Cl)$_2$ shown in FIG. 6B, mPEG(G1.5)(HO)$_2$ shown in FIG. 6C, and mPEG(G2)(Cl)$_4$ shown in FIG. 6D.
Figure 6B:
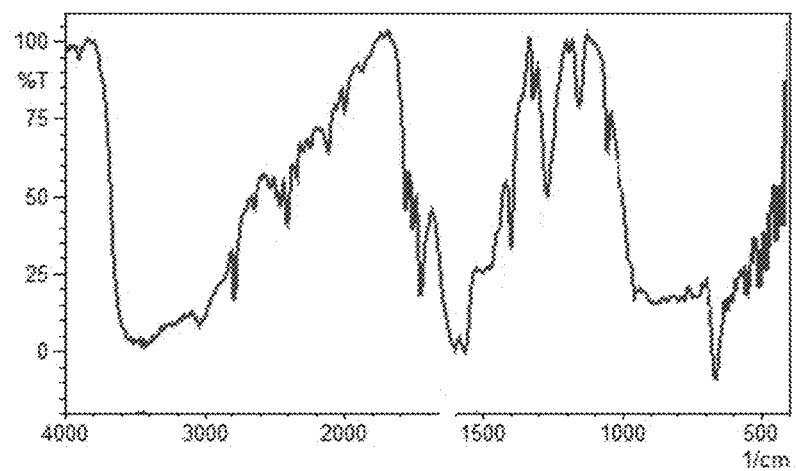
Figure 6C:
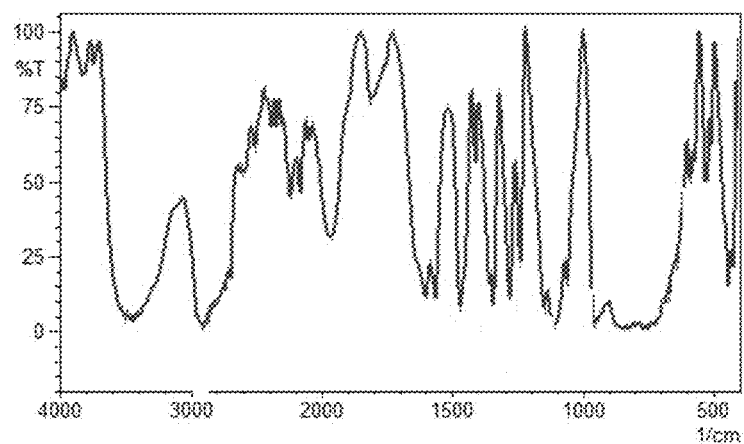
Figure 6D:
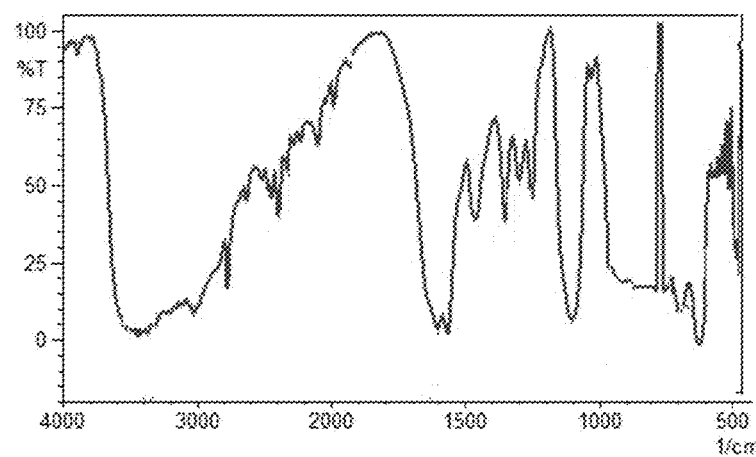

The conjugation of synthesized acetal PEG(G2)(Cl)$_8$ and lupeol is shown in FIG. 5 which depicts the coupling of lupeol to acetal PEG(G2)(Cl)$_8$ dendrimer by reacting lupeol to the acetal PEG(G2)(Cl)$_8$ dendrimer dissolved in toluene in the presence of NaHCO$_3$, stirred at room temperature for 72 h.

Example 3

Chemical Characterisation of the Dendrimers

During synthesis, the growth of dendrimer is preliminarily detected by its water solubility, color and by TLC. All the generations G1, G1.5, G2 dendrimers are freely soluble in water and white in color. This is due to the presence of mPEO as the core which enables the aqueous solubility of the different generations. TLC plates are run for identifying the consumption of reactants and formation of products. In G1, G2 dendrimers, chlorine groups are present on the periphery. However, in the core and G1.5 dendrimer, hydroxyl groups are present on periphery. This is the basic difference in the structure of different generation of dendrimers. The core and the G 1.5 shows the O—H strech at 3500 and at 3388 cm$^{-1}$ however the C—Cl strech is missing in this case. With regards to G1 and G2, the C—Cl stretching is detected at 586 and 580 cm$^{-1}$ and the O—H strech is not visible (See FIGS. 6A-6D).

The different generations of PEG dendrimers have been characterized physicochemically as mentioned above and the practical description of each generation and intermediates is given in Table 1.

TABLE 1

Physicochemical characterization of the different generations of the PEG dendrimers

| Dendrimer generation | Appearance Colour/form | Theoretical $M_W$ | Aqueous solubility | Group at periphery |
|---|---|---|---|---|
| mPEG(G1) | White/solid | 5184 | Soluble | Cl(2) |
| mPEG(G1.5) | White/solid | 11,884 | Soluble | OH(2) |
| mPEG(G2) | White/solid | 12,258 | Soluble | Cl(4) |
| Acetal PEG(G1) | White/solid | 533 | Soluble | Cl(4) |
| Acetal PEG(G1.5) | White/solid | 13,933 | Soluble | OH(4) |
| Acetal PEG(G2) | White/solid | 14,670 | Soluble | Cl(8) |

Example 4

Determination of Cytotoxicity

Cell Culture

Human prostate cancer cells (PC-3 cells) are obtained from NCCS, Pune, India. The cells are grown in RPMI 1640 medium supplemented with 10% of bovine fetal serum and antibiotics (100 IU of penicillin/100 mg/mL of streptomycin). The cells are maintained in a 25 cm$^2$ T-flask and incubated at 37° C. under 5% CO$_2$ in a humidified atmosphere. The cell viability is measured by staining the cells with trypan blue and counted in a haemocytometer under a light microscope.

Determination of Cytotoxicity

The cytotoxicity assay [MTT assay] is performed in a 96-well microtitration plate. Cells are seeded at a density of approximately 5*1000 cells/well. The plate is then incubated at 37° C., 5% CO$_2$ and 90% humidity for 24 h. Subsequently, different concentrations of free lupeol, lupeol-dendrimer conjugate and doxorubicin as positive control are added to the appropriate wells. Negative control wells with no compound are also included. The assay is performed in triplicates.

MTT Assay

The cytotoxicity is quantitatively estimated by a non-radioactive, colorimetric assay system using a tetrazolium salt, 3-[4,5-dimethylthiazol-2-yl]-2,5-diphenil-tetrazolium bromide (MTT). MTT is dissolved in phosphate-buffered saline at 5 mg/mL. MTT solution is then added directly to all appropriate microtitre plate wells (10 µL per 100 µL medium) containing cells and complete growth medium, with or without the test compound. The plate is then incubated for 4 hrs at 37° C. to allow MTT to metabolize to formazan. Subsequently, the supernatant is aspirated and 100 µL of DMSO is added and mixed thoroughly to dissolve the dark blue formazan crystals. The optical density (OD) is measured at 570 nm and 620 nm as reference is recorded in an ELISA plate reader (FLUO star OPTIMA).

Results

The cytotoxic effect of lupeol and the dendrimer lupeol conjugate is determined using PC3 cells. The comparison of the percentage inhibition of free lupeol, mPEG(G2)-lupeol conjugate, acetal PEG(G2)-lupeol conjugate, mPEG(G2) dendrimer alone and acetal PEG(G2) dendrimer alone is done using MTT assay. Doxorubicin is used as positive control for each experiment. At a concentration of 10 µg/ml and 48 hrs of treatment, it is observed that free lupeol shows an inhibition activity of only 7.74%, in comparison to the inhibition of 19.9% and 31.5% showed by mPEG(G2)-lupeol conjugate and acetal PEG(G2)-lupeol conjugates respectively. The cytotoxic effect of the dendrimer alone is tested and it is observed that they show no growth inhibition as illustrated in FIG. 7. This clearly showcases that the increase in cytotoxic activity of the dendrimer-lupeol conjugate is not due to the dendrimer or lupeol alone but because of the conjugate of dendrimer and lupeol.

Example 5

Materials Used

Succinic anhydride, Folic acid, N,N-Dicyclohexaylcarbodimide(DCC) were purchased from Sigma Aldrich.

Triethyl amine (TEA) was purchased from Avrasynthesis, doxorubicin hydrochloride injection from Pfizer, 4-(dimethylamino pyridine) (DMAP) was purchased from Merck, and N-Hydroxysuccinimide (NHS), Tetra Hydrofuran (THF), Dimethyl sulphoxide (DMSO) and Trifluroacetic acid (TFA) was purchased from Sisco research laboratories (SRL)

Coupling of Doxorubicin to mPEG(G2.5)(OH)$_4$

Figure 9:
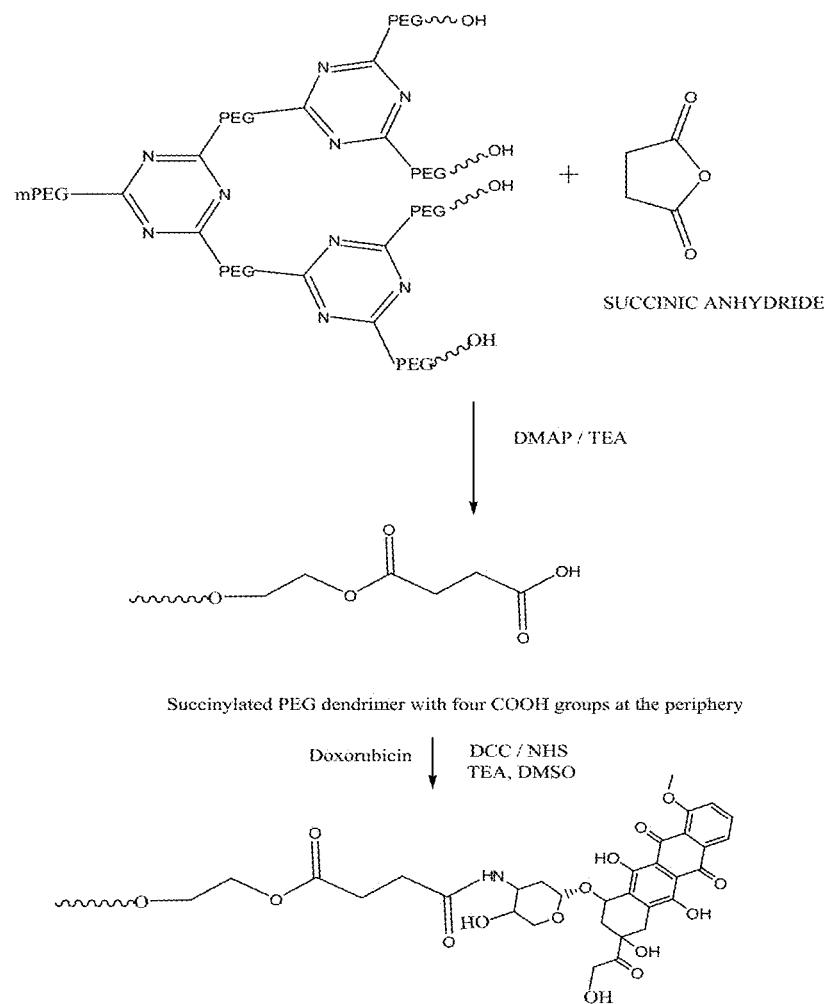
FIG. 9 illustrates the overall synthesis of mPEG(G2.5) dendrimer-doxorubicin conjugate via two step reaction. Step one involving the synthesis of succinylated mPEG(G2.5) dendrimer by reacting mPEG(2.5) dendrimer with succininc anhydride in the presence of DMAP/TEA. Step two involves reaction of doxorubicin dissolved in DMSO to the succinylated mPEG(G2.5) dendrimer in the presence of DCC/NHS and TEA.

The FIG. 9 illustrates the overall synthesis of mPEG (G2.5)—doxorubicin conjugate.

Synthesis of succinylated PEG dendrimer from mPEG(G2.5)(OH)$_4$ (mPEG(G2.5)(COOH)$_4$)

0.1 mmol of succinic anhydride is dissolved in 20 ml THF containing 0.1 mmol of DMAP. This solution is kept at 0° C.-4° C. for 30 mins. A solution of 0.019 mmol of mPEG (G2.5)(OH)$_4$ dissolved in 45 ml of THF containing 0.1 mmol of TEA is added dropwise to the above solution. The mixture is then stirred at 0° C.-4° C. for 2 hr and at room temperature overnight. At the end of the reaction, the solution is dried and then dissolved in dichloromethane and filtered to remove unreacted succinic anhydride. The solution is concentrated and precipitated using cold diethyl ether. The precipitated product is dried under vacuum.

Conjugation of doxorubicin to mPEG(G2.5)(COOH)$_4$ i.e. (mPEG(G2.5)-Doxorubicin conjugate.

The 0.012 mmol of succinylated mPEG(G2.5)(COOH)$_4$ dendrimer is dissolved in 2 ml DMSO containing 0.13 mmol of NHS, 0.041 mmol of DCC, and 0.072 mmol of TEA. To this solution, 0.06 mmol of doxorubicin is added under nitrogen atmosphere and stirred overnight at 25° C.-30° C. At the end of the reaction time, the reaction mixture is dialysed against water for 4 hr with three water changes to remove the unreacted free doxorubicin. This product is obtained as lyophilised powder.

Coupling of Doxorubicin to acetal PEG(G2.5)(OH)$_8$

Figure 10:
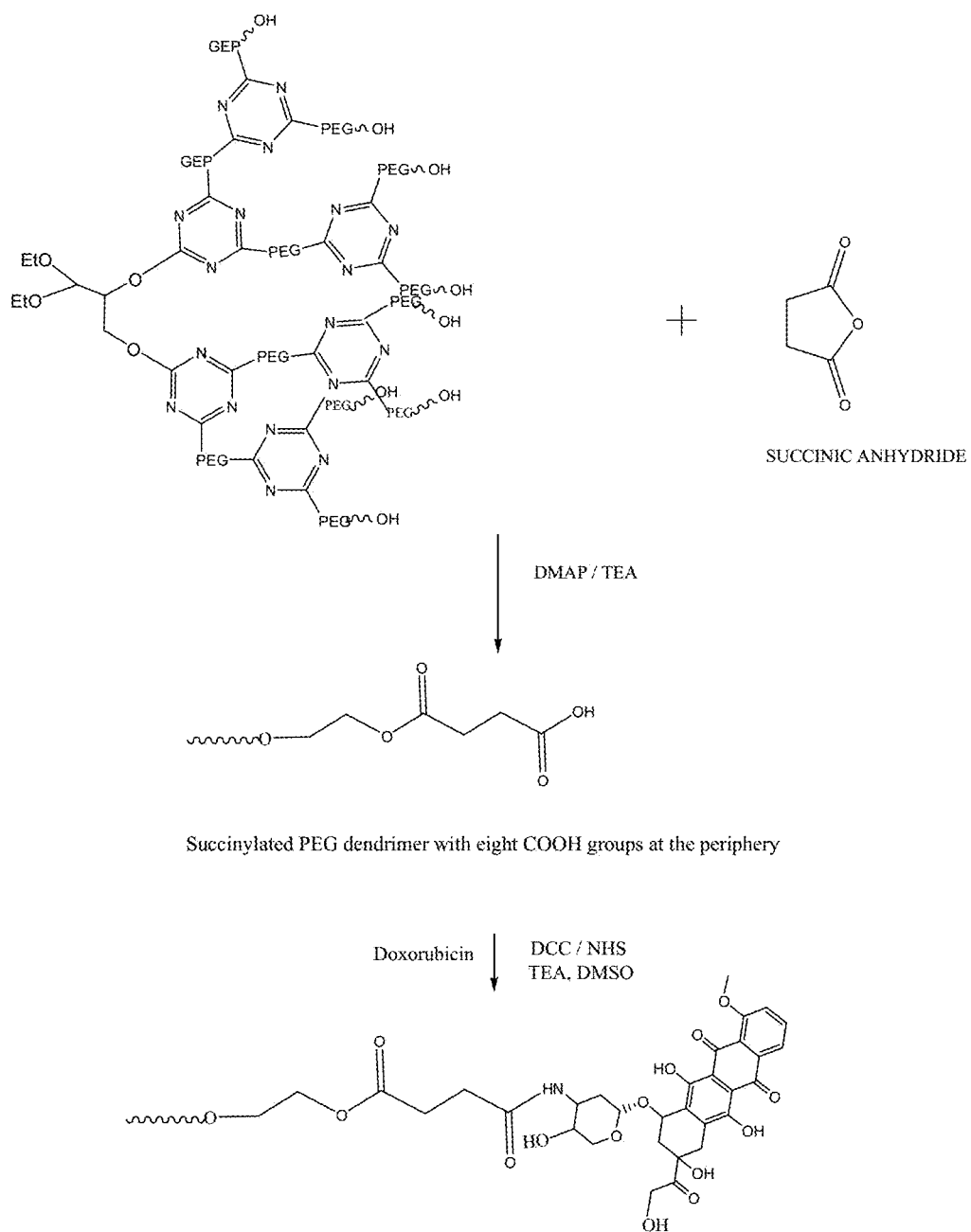
FIG. 10 illustrates the overall synthesis of acetal (G2.5) dendrimer-doxorubicin conjugate via two step reaction. Step one involving the synthesis of succinylated acetal(G2.5) dendrimer by reacting acetal(2.5) dendrimer with succininc anhydride in the presence of DMAP/TEA. Step two involves reaction of doxorubicin dissolved in DMSO to the succinylated acetal(G2.5) dendrimer in the presence of DCC/NHS and TEA.

The FIG. 10 illustrates the overall synthesis of acetal PEG(G2.5)-doxorubicin conjugate.

Synthesis of Succinylated PEG Dendrimer from Acetal(G2.5)(OH)$_8$ (Acetal(G2.5)(COOH)$_8$)

0.8 mmol of succinic anhydride is dissolved in 20 ml THF containing 0.72 mmol of DMAP. This solution is kept at 0° C.-4° C. for 30 mins. A solution of 0.009 mmol of acetal (G2.5)(OH)$_8$ dissolved in 45 ml of THF containing 0.72 mmol of TEA is added drop wise to the above solution. The mixture is then stirred at 0° C.-4° C. for 2 hr and at room temperature for overnight. At the end of the reaction, the solution is dried and then dissolved in dichloromethane and filtered to remove unreacted succinic anhydride. The solution is then concentrated and precipitated using cold diethyl ether. The precipitated product is dried under vacuum.

Conjugation of doxorubicin to acetal(G2.5)(COOH)$_8$ i.e. (acetal-PEG(G2.5)-Doxorubicin conjugate The $0.2^{-4}$ mmol of succinylated acetal(G2.5)(COOH)$_8$ dendrimer is dissolved in 2 ml DMSO containing 0.11 mmol of NHS, 0.019 mmol of DCC, and 0.072 mmol of TEA. To this solution 0.007 mmol of doxorubicin is added under nitrogen atmosphere and stirred overnight at 25° C.-30° C. At the end of the reaction time the reaction mixture is dialysed against water for 4 hr with three water changes to remove the unreacted free doxorubicin. This product is obtained as lyophilised powder.

Similar conjugation is also done for acetal(G1.5)(OH)$_4$ to study the effect of ligand (i.e drug) density and distribution.

Example 6

Targeted Delivery of the Acetal PEG (G2.5)-Doxorubicin Conjugate and Acetal PEG(G1.5)-Doxorubicin Conjugate Using Folic Acid Folic acid is used to target cancer cells as the cancer cells are known to overexpress folic acid receptors. This reaction is done for the acetal PEG (G2.5)(OH)$_8$ and acetal PEG (G1.5)-doxorubicin conjugate dendrimers as the free acetal group on one side of the dendrimer is converted to aldehyde group, which in turn is used to couple folic acid.

This helps in targeting over expressed folic acid receptors in the cancer cells. However in case of mPEG(G2.5)-doxorubicin, the free methoxy group is unreactive in nature and thus its conversion to a reactive group requires very harsh conditions.

Figure 11:
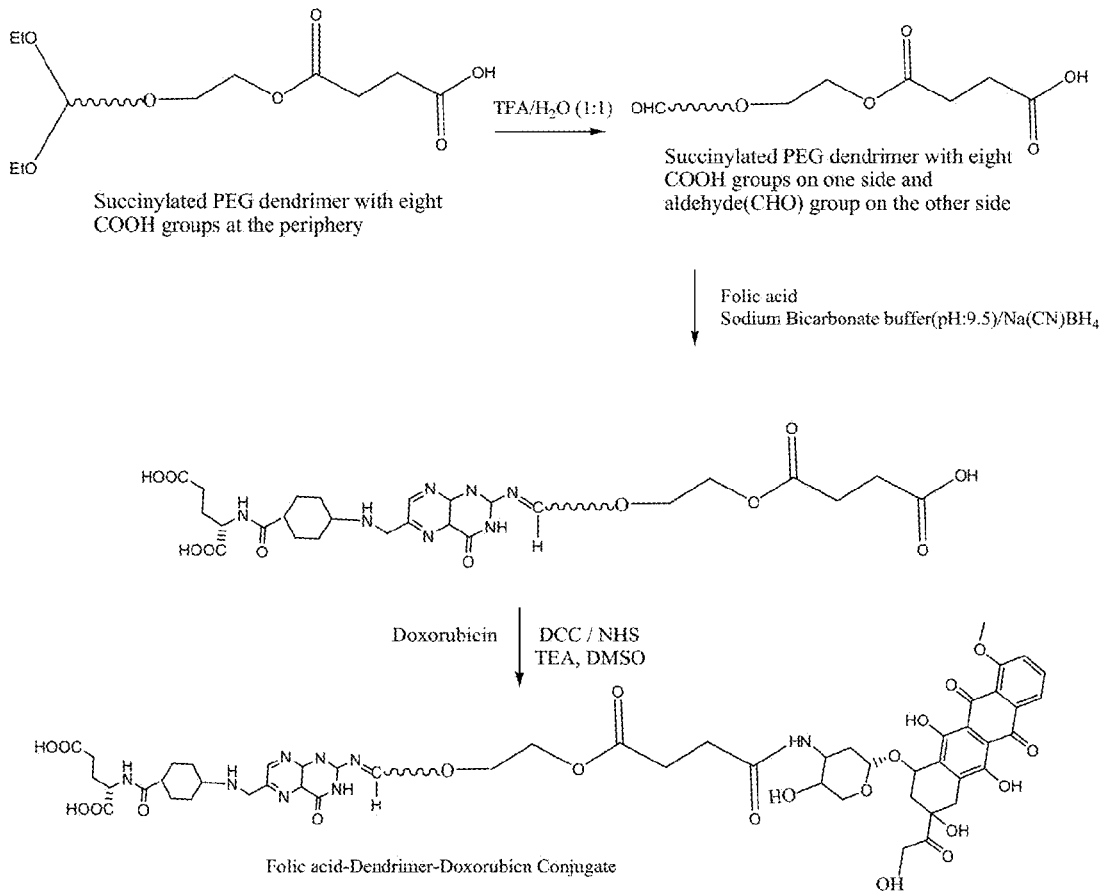
FIG. 11 illustrates the overall synthesis of Folic acid-acetal (G2.5) dendrimer-doxorubicin conjugate for targeted delivery of doxorubicin.

FIG. 11 illustrates the Synthesis of Folic acid-dendrimer (2.5)-Doxorubicin conjugate for targeted delivery.

Synthesis of Targeted Acetal PEG(G2.5)-Doxorubicin Conjugate with Folic Acid as the Targeting Moiety Conversion of Acetal Group of Acetal(G2.5)(COOH)$_8$ to Active Aldehyde Group for Coupling to Folic Acid.

0.2 g of succinylated acetal(G2.5)(COOH)$_8$ dendrimer is refluxed with 8 ml of TFA:H$_2$O(1:1) at 65° C.-70° C. for 20 hr. The solution is concentrated and extracted using 50 ml-60 ml of dichloromethane. The combined organic layers are concentrated and precipitated using diethyl ether. The precipitate is dried under vacuum. The reaction is monitored for the complete conversion of acetal group to aldehyde group using TLC.

Conjugation of Folic Acid to Activated Acetal(G2.5) Dendrimer (FA-PEG(G2.5)-(COOH)$_8$)

6 mg (0.013 mmol) of folic acid is added to 2 ml of sodium bicarbonate buffer (pH 9.5) containing 20 mg activated aldehyde activated acetal(G2.5) dendrimer. The solution is stirred for 2 hr at 25° C.-30° C. for 2 hr. To this solution 80 µl of 0.5M sodium cyanoborohydride is added in dark and stirred overnight. At the end of the reaction time, the reaction mixture is dialysed against water for 4 hr, three water changes to remove unreacted free folic acid. The final product is obtained as lyophilised powder.

Conjugation of Doxorubicin to FA-PEG(G2.5)-(COOH)$_8$ i.e. (FA-PEG(G2.5)-Doxorubicin Conjugate.

The $0.2^{-4}$ mmol of FA-PEG(G2.5)-(COOH)$_8$ dendrimer is dissolved in 2 ml DMSO containing 0.11 mmol of NHS, 0.019 mmol of DCC, and 0.072 mmol of TEA. To this solution 0.007 mmol of doxorubicin is added under nitrogen atmosphere and stirred overnight at 25° C.-30° C. At the end of the reaction time the reaction mixture is dialysed against water for 4 hr with three water changes to remove the unreacted free doxorubicin. The product is obtained as lyophilised powder.

Similarly conjugation of Folic acid is also done for acetal PEG(G1.5)(OH)$_4$.

Determination of Cytotoxicity:

The cytotoxic effect of doxorubicing dendrimer conjugate is studied on PC3 i.e. Prostate cancer cell line and HCT i.e. human colon cancer cell line.

Determination of Cytotoxicity

The cytotoxicity assay [MTT assay] is performed in a 96-well microtitration plate. Cells are seeded at a density of approximately 5*1000 cells/well. The plate is then incubated at 37° C., 5% CO2, and 90% humidity for 24 h. Subsequently, different concentrations of free lupeol, lupeol-dendrimer conjugate and doxorubicin as positive control are added to the appropriate wells. Negative control wells with no compound are also included. The assay is performed in triplicates.

MTT Assay

The cytotoxicity is quantitatively estimated by a non-radioactive, colorimetric assay system using a tetrazolium salt, 3-[4,5-dimethylthiazol-2-yl]-2,5-diphenil-tetrazolium bromide (MTT). MTT is dissolved in phosphate-buffered saline at 5 mg/mL. MTT solution is then added directly to all appropriate microtitre plate wells (10 µL per 100 µL medium) containing cells and complete growth medium, with or without the test compound. The plate is then incubated for 4 hours at 37° C. to allow MTT to metabolize to formazan. Subsequently, the supernatant is aspirated and 100 µL of DMSO is added and mixed thoroughly to dissolve the dark blue formazan crystals. The optical density (OD) is measured absorbance at 570 nm and 620 nm as reference is recorded in an ELISA plate reader (FLUO star OPTIMA).

Results:

Cytotoxicity of free Doxorubicin, Dendrimer-doxorubicin conjugates (a) and Folic acid-dendrimer doxorubicin conjugates (for targeting) (b) were studied on PC3 prostate cancer cells and HCT-15 human colon cancer cells. The amount of doxorubicin in the conjugates (a) and (b) is calculated spectrophotometrically. Cells are incubated for 48 hr with different equivalent doxorubicin concentrations and IC$_{50}$ values in terms of doxorubicin were calculated using MTT assay.

Figure 12:
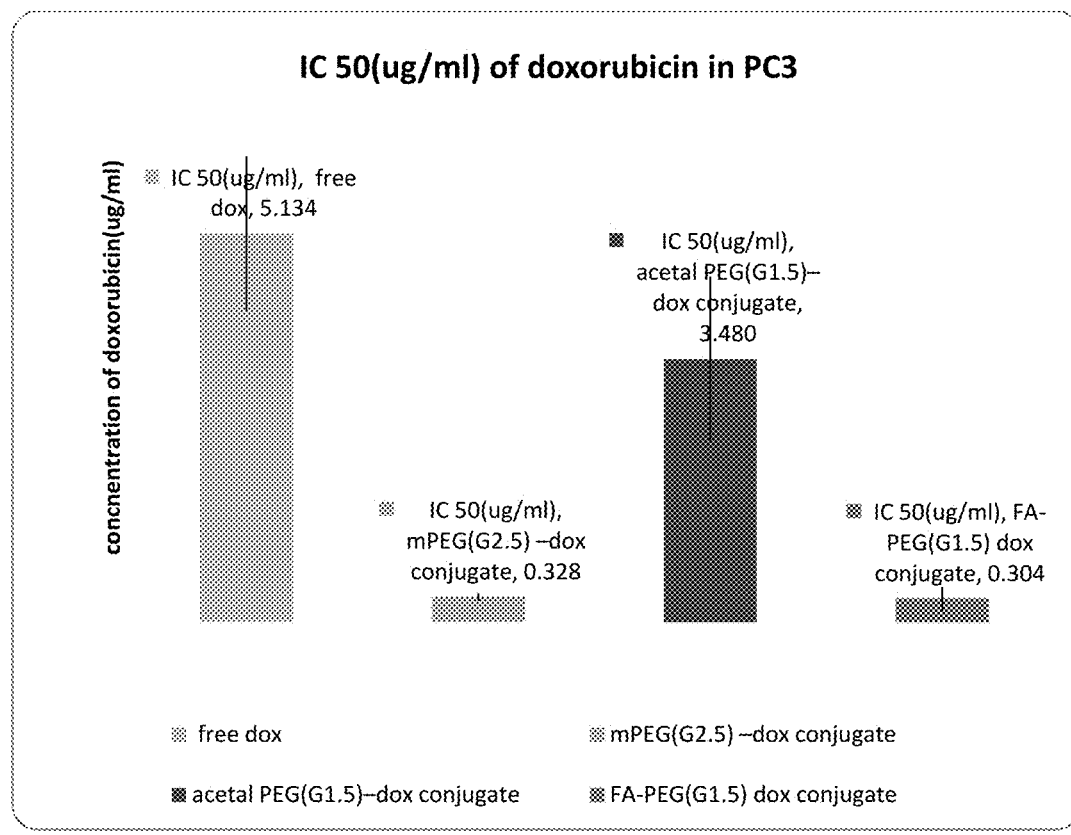
FIG. 12 illustrates the comparison of IC50 value of free doxorubicin, mPEG(G2.5)-doxorubicin conjugate, acetal PEG(1.5)-doxorubicin conjugate, acetal PEG(G1.5)-doxorubicin conjugate targeted using folic acid (FA-PEG(G1.5)-doxorubicin in PC3 cell line at 48 hr of treatment.
Figure 13:
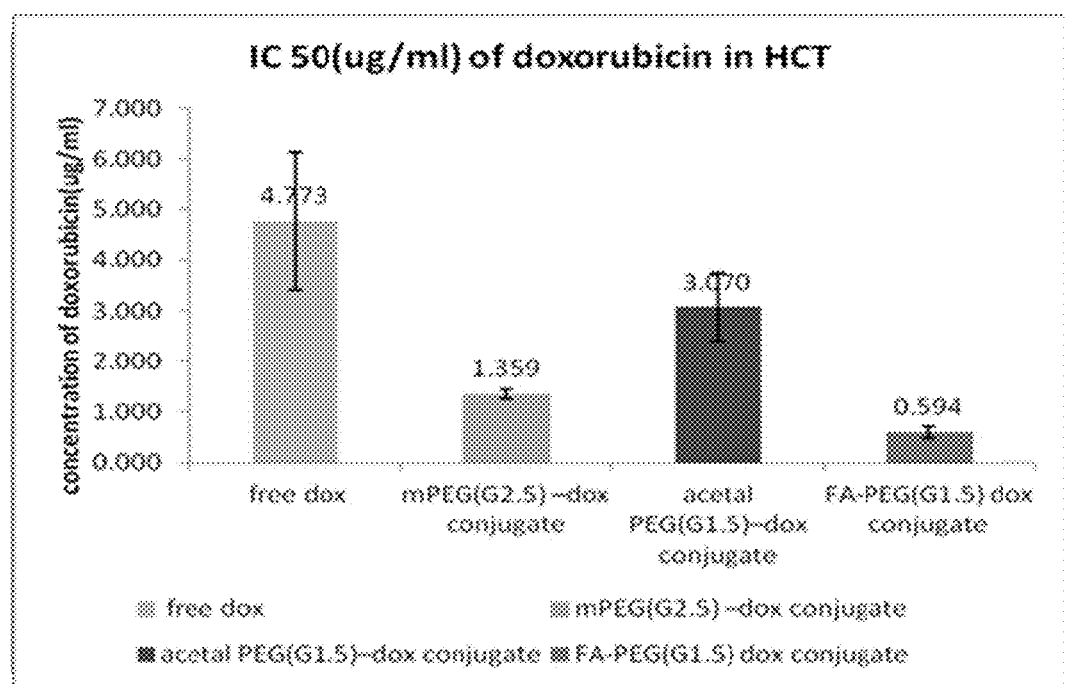
FIG. 13 illustrates the comparison of IC50 value of free doxorubicin, mPEG(G2.5)-doxorubicin conjugate, acetal PEG(1.5)-doxorubicin conjugate, acetal PEG(G1.5)-doxorubicin conjugate targeted using folic acid (FA-PEG(G1.5)-doxorubicin HCT-15 cell line at 48 hr of treatment.

FIGS. 12 and 13 illustrate the comparison of IC$_{50}$ value of free doxorubicin, mPEG(G2.5)-doxorubicin conjugate, acetal PEG(1.5)-doxorubicin conjugate, acetal PEG(G1.5)-doxorubicin conjugate targeted using folic acid (FA-PEG (G1.5)-doxorubicin in PC3 cell line and HCT-15 cell line at 48 hr of treatment respectively. The IC$_{50}$ values are given in equivalent doxorubicin concentration.

Figure 14:
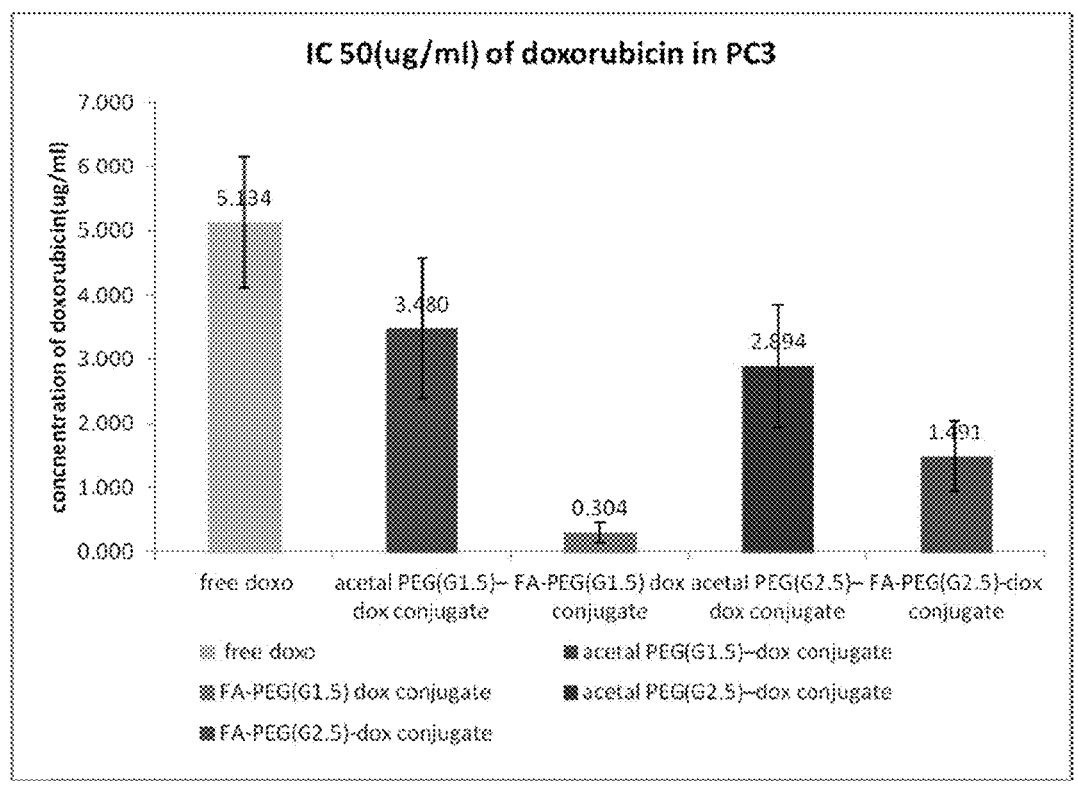
FIG. 14 illustrates the comparison of IC50 value of free doxorubicin, acetal PEG(G2.5)-doxorubicin conjugate, acetal PEG(G2.5)-doxorubicin conjugate targeted using folic acid (FA-PEG(G2.5)-doxorubicin), acetal PEG(1.5)-doxorubicin conjugate, acetal PEG(G1.5)-doxorubicin conjugate targeted using folic acid (FA-PEG(G1.5)-doxorubicin in PC3 cell line at 48 hr of treatment.
Figure 15:
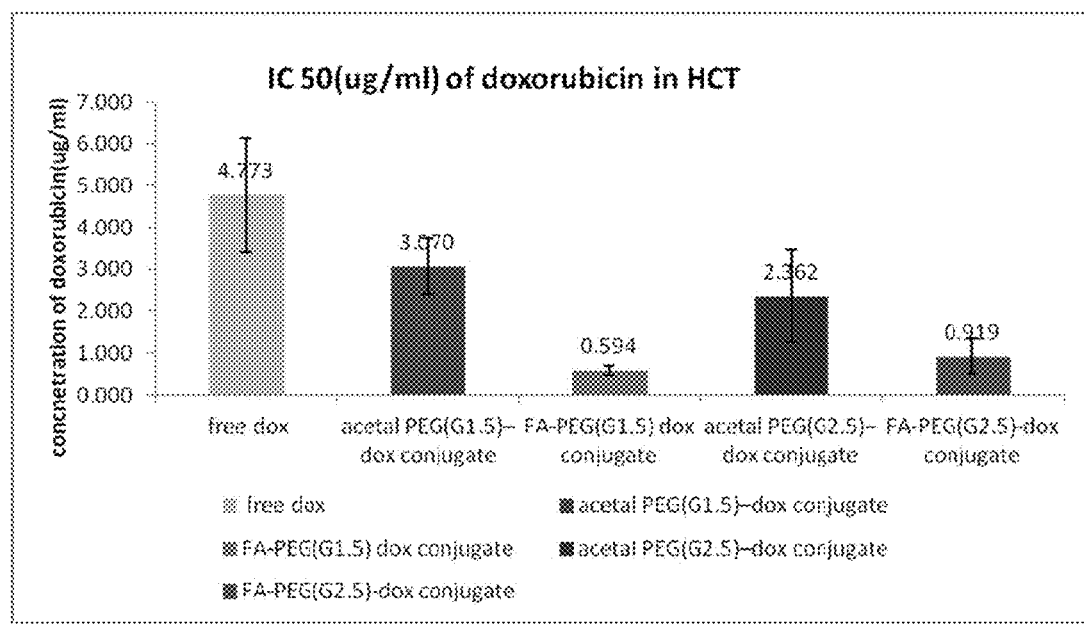
FIG. 15 illustrates the comparison of IC50 value of free doxorubicin, acetal PEG(G2.5)-doxorubicin conjugate, acetal PEG(G2.5)-doxorubicin conjugate targeted using folic acid (FA-PEG(G2.5)-doxorubicin, acetal PEG(1.5)-doxorubicin conjugate, acetal PEG(G1.5)-doxorubicin conjugate targeted using folic acid (FA-PEG(G1.5)-doxorubicin in HCT-15 cell line at 48 hr of treatment.

FIGS. 14 and 15 illustrate the comparison of IC$_{50}$ value of free doxorubicin, acetal PEG(G2.5)-doxorubicin conjugate, acetal PEG(G2.5)-doxorubicin conjugate targeted using folic acid (FA-PEG(G2.5)-doxorubicin), acetal PEG(1.5)-doxorubicin conjugate, acetal PEG(G1.5)-doxorubicin conjugate targeted using folic acid (FA-PEG(G1.5)-doxorubicin in PC3 cell line and HCT-15 cell line at 48 hr of treatment respectively. The IC$_{50}$ values are given in equivalent doxorubicin concentration.

DISCUSSION

Cytotoxicity of free doxorubicin, mPEG(G2.5)-doxorubicin conjugate, acetal PEG(G1.5)-doxorubicin conjugate, FA-PEG(G1.5)-doxorubicin conjugate are compared using MTT assay. All the three dendrimers conjugated to the doxorubicin have same number of hydroxyl groups (i.e. four) at the periphery for conjugation. The IC$_{50}$ values of the free and the conjugated drug (both targeted and non-targeted) were calculated and compared after 48 hr treatment. All the results are expressed in terms of IC$_{50}$ values of equivalent doxorubicin concentration.

The IC$_{50}$ values in µg/ml of the free and the conjugated doxorubicin in PC3 and HCT15 cell lines are given below:

TABLE 2

IC$_{50}$ values of free doxorubicin and mPEG(G2.5)-doxorubicin conjugate, acetal PEG(1.5)-doxorubicin conjugate, acetal PEG(G1.5)-doxorubicin conjugate targeted using folic acid (FA-PEG(G1.5)-doxorubicin conjugate in PC3 and HCT-15 cell line after 48 hr of treatment. (FIGS. 12 and 13)

| Cytotoxic molecule | PC3 | HCT-15 |
| --- | --- | --- |
| Free doxorubicin | 5.134 µg/ml | 4.773 µg/ml |
| mPEG(G2.5)-doxorubicin conjugate | 0.328 µg/ml | 1.350 µg/ml |
| Acetal PEG(G1.5)-doxorubicin conjugate | 3.480 µg/ml | 3.070 µg/ml |
| FA-PEG(G1.5)-doxorubicin conjugate | 0.304 µg/ml | 0.594 µg/ml |

The lower the IC$_{50}$ value, the more is the cytotoxic activity of the bioactive molecule.

1) The results show a significant difference in the cytotoxicity of the free doxorubicin to that of the conjugated doxorubicin.
2) The cytotoxicity of free doxorubicin and the two non-targeted dendrimer-doxorubicin conjugates i.e. mPEG (G2.5)-doxorubicin conjugate and Acetal PEG(G1.5)-doxorubicin conjugates were compared. Both the conjugates showed an increased cytotoxicity as compared to that of free doxorubicin.
3) On comparing the targeted FA-PEG(G1.5)-doxorubicin conjugate and the non-targeted acetal PEG(G1.5)-doxorubicin conjugate, a significant increase in cytotoxicity was observed in the targeted conjugate when compared to the free drug and the non-targeted conjugate.

To understand the effect of drug density and distribution of the cytotoxic molecule, the effect of conjugation of the drug to two different generations of the acetal-PEG dendrimer i.e acetal PEG(G1.5)(OH)$_4$ with four functional groups present on the periphery for conjugation and acetal PEG(G2.5)(OH)$_8$ with eight functional groups present on the periphery for conjugation are compared.

TABLE 3

IC$_{50}$ values in µg/ml of free doxorubicin, acetal PEG(1.5)-doxorubicin conjugate, acetal PEG(G1.5)-doxorubicin conjugate targeted using folic acid (FA-PEG(G1.5)-doxorubicin acetal PEG(G2.5)-doxorubicin conjugate, FA-PEG(G2.5)-doxorubicin conjugate in PC3 cells and HCT-15 cells after 48 hr treatment as described in FIGS. 14 and 15.

| Cytotoxic molecule | PC3 | HCT-15 |
|---|---|---|
| Free doxorubicin | 5.134 µg/ml | 4.773 µg/ml |
| Acetal PEG(G1.5)-doxorubicin conjugate | 3.480 µg/ml | 3.070 µg/ml |
| FA-PEG(G1.5)-doxorubicin conjugate | 0.304 µg/ml | 0.504 µg/ml |
| AcetalPEG(G2.5)-doxorubicin conjugate | 2.894 µg/ml | 2.362 µg/ml |
| FA-PEG(G2.5)-doxorubicin conjugate | 1.491 µg/ml | 0.920 µg/ml |

The comparison of IC50 value of free doxorubicin and the two non-targeted conjugates acetal PEG(G2.5)-doxorubicin conjugate (with eight functional groups), and acetal PEG(G1.5)-doxorubicin conjugate (with four functional groups) showed a significant increase in the cytotoxicity of the conjugated doxorubicin as compared to the free doxorubicin.

In the case of acetal PEG(G2.5)-doxorubicin conjugate (with eight functional groups), the increase was more as compared to the acetal PEG(G1.5)-doxorubicin conjugate (with four functional groups). This difference may be attributed to the high drug density in case of acetal PEG(G2.5)-doxorubicin conjugate when compared to acetal PEG(G1.5)-doxorubicin conjugate.

The conjugation of folic acid as the targeting moiety to both the dendrimer-doxorubicin conjugates showed a further increase in cytotoxicity when compared to non-targeted conjugates. However, in case of targeted conjugates, it was observed that the increase in cytotoxic activity was more in FA-PEG(G1.5)-doxorubicin conjugate when compared to FA-PEG(G2.5)-doxorubicin conjugate. This can be attributed to the high density of doxorubicin thereby, reducing the interaction between the target and the targeting moiety due to steric hindrance.

The results of the MTT assay clearly showed that the cytotoxic activity of doxorubicin significantly increased on conjugating to the dendrimer. Also a significant increase in the cytotoxic activity was seen in case of the targeted and the non-targeted dendrimer-doxorubicin conjugates.

Advantages:

The conjugation of drugs to dendrimers results in decreased non-specific toxicity, enhanced therapeutic efficacy, optimized drug bio-distribution, increased circulation time in blood, and targeted drug delivery. The more number of functional groups on the outer shell of dendrimers result in high reactivity and due to the same, the dendrimer conjugate with a series of bioactive molecules. Further, there is a rapid penetration of dendrimer-drug conjugates with a high drug payload into the cells and hence their localization in the cytoplasm or nucleous. Conjugation of drugs to dendrimers increases the activity of the attached drugs by EPR (enhanced permeability and retention) effect.

In a further embodiment, the present disclosure relates to bouquet type dendrimers, synthesised using monomethoxy PEG(5000) or 3,3diethoxy-1,2-propanediol as cores. The branching units in both the dendrimers are triazine trichloride and PEG(3350). The synthesis of these dendrimers is simple and cost effective. The dendrimers disclosed in the present disclosure is used as a carrier and thus conjugated with known bioactive molecules/drugs to form conjugates. The conjugation of these dendrimers to bioactive molecule lupeol known for its anticancer activity shows a significant increase in the cytotoxic activity as compared to free lupeol.

Therefore, the present disclosure provides an alternate treatment for cancer using PEG based dendrimers as drug carriers and exploiting the potentials of plant based bioactive molecules resulting in enhanced efficacy, bioavailability and reduced toxicity.

Further, the present disclosure makes use of different core groups such as methoxy PEG and 3,3-diethoxy-1,2-propanediol respectively and consist of dihydroxy poly(ethylene oxide) i.e., PEG and triazine trichloride as branching units in their structural frame.

Further, the active functional groups such as chloride groups on the triazine ring can be used to conjugate drug molecules as shown in case for lupeol conjugation. Similarly, the hydroxyl groups on the PEG can be used for drug conjugation as shown for doxorubicin. The group available for conjugation depends on the generation of the dendrimer used.

In case of the conjugation through hydroxyl group —OH, modification of the hydroxyl group (OH) to a more reactive acidic group (COOH) is used. The COOH group is then used for conjugation with doxorubicin.

In an embodiment of the present disclosure, modifications can be done to the —OH group in order to conjugate a number of drug molecules. Few examples of the modification are given below:

Conversion of hydroxyl group to amine (NH2) group;
Conversion of hydroxyl group to chloride groups using Tosyl chloride, wherein the active chloride groups provide for conjugation;
Conversion of hydroxyl group to aldehyde group (CHO); and
Conversion of hydroxyl group to carboxylic group (COOH).

The hydroxyl group(s) of PEG is/are activated with maleimide group. The maleimide group is spontaneously reactive with sulfhydryl (SH) group, thus easily conjugating to thiol containing molecules.

In another embodiment of the present disclosure, substituents used for activation of hydroxyl group for biological and biotechnical applications are selected from, but not limiting to trifluoroethylsulfonate (tresylate), n-hydroxylsuccinimide ester, cyanuric fluoride, acyl azide, succinate, p-diazo benzyl group and 3-(p-diazophenyloxy)-2-hydroxy propyloxy group.

We claim:

1. A dendrimer having the following formula:

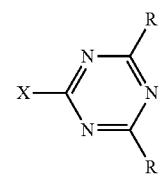

wherein X is selected from the group consisting of

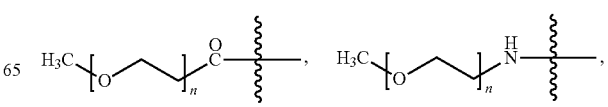

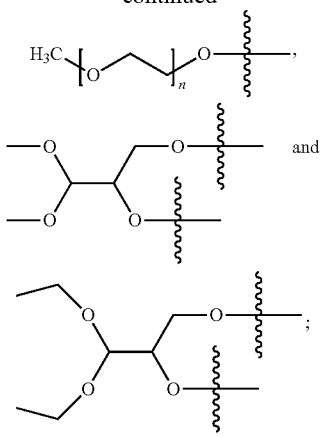

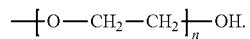

wherein n is 1-50; and
wherein R is selected from the group consisting of Cl, F, —OH and $-[O-CH_2-CH_2-]_n OH$ when said dendrimer is one of a generation 1 dendrimer or a generation 1.5 dendrimer; and
wherein R is $R_d$ when said dendrimer is any one of a generation 2-10 dendrimer, said $R_d$ having the following formula:

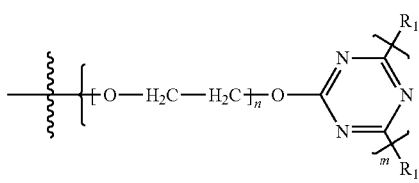

wherein m is 1-9; $R_1$ is selected from the group consisting of Cl, F and —OH; and
wherein said dendrimer includes an active functional group of a periphery thereof, said active functional group selected from the group consisting of Cl, F, —OH, and

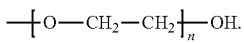

2. The dendrimer as claimed in claim 1, wherein said dendrimer includes one of 2, 4, 8, 16, 32, 64, 128, 256, 512, or 1024 active functional groups.

3. A method of obtaining a methoxy PEG generation 2 dendrimer of claim 1, having four active groups, said method comprising the steps of:
reacting methoxy PEG with an aromatic heterocycle to obtain a methoxy PEG generation 1 dendrimer having two active groups;
reacting the methoxy PEG generation 1 dendrimer having two active groups with dihydroxy PEG to obtain a methoxy PEG generation 1.5 dendrimer having two active groups; and
reacting the methoxy PEG generation 1.5 dendrimer having two active groups with an aromatic heterocycle to obtain said methoxy PEG generation 2 dendrimer having four active groups,
wherein the active groups are selected from the group consisting of a hydroxyl group (—OH), chloride, fluoride, and $-[O-CH_2-CH_2-]_n OH.$ 4. The method as claimed in claim 3, wherein the aromatic heterocycle is one of triazine trichloride and 2,4,6-trifluoro-1,3,5-triazine.

5. The method as claimed in claim 3, wherein the reacting steps are carried out in the presence of sodium bicarbonate and toluene.

6. A method of obtaining acetal PEG generation 2 dendrimer of claim 1 having eight active functional groups, said method comprising the steps of:
reacting 3,3-diethoxy-1,2-propanediol with a first aromatic heterocycle to obtain an acetal PEG generation 1 dendrimer having four active functional groups;
reacting the acetal PEG generation 1 dendrimer having four active functional groups with PEG to obtain an acetal PEG generation 1.5 dendrimer having four active functional groups; and
reacting the acetal PEG generation 1.5 dendrimer having four active functional groups with a second aromatic heterocycle to obtain said acetal PEG generation 2 dendrimer having eight active functional groups.

7. The method as claimed in claim 6, wherein first and second aromatic heterocycles are aromatic heterocycles selected from the group consisting of triazine trichloride and 2,4,6-trifluoro-1,3,5-triazine; and further wherein the active functional groups are active functional groups selected from the group consisting of a hydroxyl group (—OH), chloride, fluoride, and

8. The method as claimed in claim 6, wherein the reacting steps are carried out in the presence of sodium bicarbonate and toluene.

9. A conjugate consisting of the dendrimer as claimed in claim 1 and a bioactive molecule; wherein the dendrimer is optionally linked to a targeting agent.

10. The conjugate as claimed in claim 9, wherein the bioactive molecule or the targeting agent is covalently attached onto one of a surface of the dendrimer, an interior of the dendrimer, and a combination thereof.

11. The conjugate as claimed in claim 9, wherein the targeting agent is selected from the group consisting of monoclonal antibodies, vitamins, folic acid, peptides, and polysaccharides.

12. The conjugate as claimed in claim 11, wherein the targeting agent is folic acid.

13. A pharmaceutical composition including the conjugate as claimed in claim 9, wherein the pharmaceutical composition optionally includes one or more pharmaceutically acceptable excipients.

14. A method of inducing/increasing cytotoxicity in cancer cells, said method comprising the steps of incubating the cancer cells with the conjugate as claimed in claim 9.

15. A method of inducing/increasing cytotoxicity in cancer cells, said method comprising the steps of incubating the cancer cells with the pharmaceutical composition as claimed in claim 13.

16. A method of treating a subject having or suspecting of having cancer, said method comprising the steps of administering the conjugate as claimed in claim 9 to the subject in need thereof.

17. A method of treating a subject having or suspecting of having cancer, said method comprising the steps of administering the pharmaceutical composition as claimed in claim 13 to the subject in need thereof.

18. The conjugate as claimed in claim 9, wherein the bioactive molecule is selected from the group comprising lupeol, doxorubicin, betulinic acid, cisplatin, camptothecin, paclitaxel, and any combination thereof.

19. A dendrimer as claimed in claim 1, wherein when X is

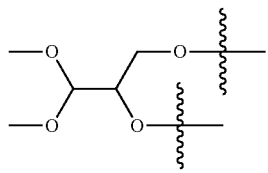

the compound is of formula

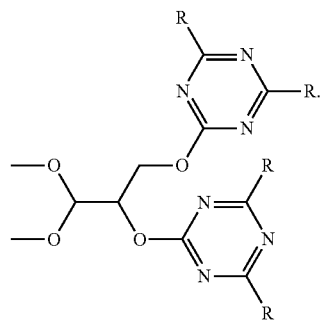

20. A dendrimer as claimed in claim 1, wherein when X is

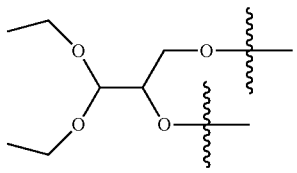 [SMILES: *OCC(O*)C(OCC)OCC]

the compound is of formula

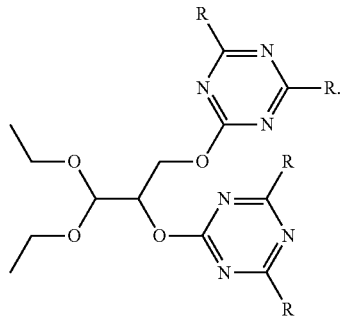

* * * * *